United States Patent
Shaw et al.

(10) Patent No.: US 9,891,232 B2
(45) Date of Patent: Feb. 13, 2018

(54) BIN1 EXPRESSION AS A MARKER OF SKELETAL MUSCLE MASS AND NEUROLOGICAL CONDITIONS

(75) Inventors: Darryl Steven Shaw, Tampa, FL (US); Neil Gavin Shaw, Odessa, FL (US)

(73) Assignee: Sarcotein Diagnostics, LLC, Tampa, FL (US)

( * ) Notice: Subject to any disclaimer, the term of this patent is extended or adjusted under 35 U.S.C. 154(b) by 289 days.

(21) Appl. No.: 13/884,454

(22) PCT Filed: Nov. 7, 2011

(86) PCT No.: PCT/US2011/059574
§ 371 (c)(1),
(2), (4) Date: Aug. 21, 2013

(87) PCT Pub. No.: WO2012/087437
PCT Pub. Date: Jun. 28, 2012

(65) Prior Publication Data
US 2013/0324432 A1 Dec. 5, 2013

Related U.S. Application Data

(60) Provisional application No. 61/411,683, filed on Nov. 9, 2010.

(51) Int. Cl.
*C40B 30/04* (2006.01)
*G01N 33/68* (2006.01)
*C07K 16/18* (2006.01)

(52) U.S. Cl.
CPC ......... *G01N 33/6887* (2013.01); *C07K 16/18* (2013.01)

(58) Field of Classification Search
CPC .................................................. G01N 33/6887
USPC .............................................................. 506/9
See application file for complete search history.

(56) References Cited

U.S. PATENT DOCUMENTS

| | | | | |
|---|---|---|---|---|
| 6,048,702 | A * | 4/2000 | Prendergast et al. | 435/7.1 |
| 7,150,968 | B2 * | 12/2006 | Prendergast | C07K 14/47 |
| | | | | 435/252.3 |
| 9,150,924 | B2 * | 10/2015 | Shaw | C07K 14/4716 |
| 2005/0260697 | A1 | 11/2005 | Wang et al. | |
| 2006/0003959 | A1 * | 1/2006 | Burden et al. | 514/44 |
| 2009/0088482 | A1 * | 4/2009 | Maybaum | A61K 31/135 |
| | | | | 514/653 |
| 2010/0086481 | A1 | 4/2010 | Baird et al. | |
| 2013/0266975 | A1 * | 10/2013 | Shaw | G01N 33/6893 |
| | | | | 435/7.92 |

FOREIGN PATENT DOCUMENTS

| WO | WO-01/04354 | A2 | | 1/2001 |
| WO | WO 0104354 | A2 | * | 1/2001 |
| WO | 2010-124240 | A2 | | 10/2010 |
| WO | WO 2010124240 | A2 | * | 10/2010 |

OTHER PUBLICATIONS

Nicot et al., Mutations in Amphiphysin 2 (BIN1) Disrupt Interation With Dynamin 2 and Cause Autosomal Recessive Centronuclear Myopathy, Nature Genetics Letters, 2007, 1134-1139.*
Fernando et al., The Journal of Biological Chemistry, 2009, 284(40), 27674-27686.*
Chang et al., Review, BIN1 (Bridging Indicator 1), Atlas of Genetics and Cytogenetics in Oncology and Haematology, 2009, 13(8), 543-548.*
MyBioSource.com, Anti-BIN1 Antibody :: Rabbit BIN1 Polyclonal Antibody, 2006, 1-4.*
Slomianka, Blue Histology—Muscle, School of Anatomy and Human Biology, The University of Western Australia, 2009, 1-14.*
Ariosa Diagnostics, Inc. v. Sequenom, Inc., Opinion of the US Court of Appeals for the Federal Circuit, 2015, 1-21.*
Nicot et al., Mutations in Amphiphysin 2 (BIN1) Disrupt Interaction With Dynamin 2 and Causes Autosomal Recessive Centronuclear Myopathy, Nature Genetics, 2007, 39(9), 1134-1139.*
Toussaint et al., Defects In Amphiphysin 2 (BIN1) and Triads In Several Forms of Centronuclear Myopathies, Acta Neuropathol, 2011, 121, 253-266.*
Lee et al., "Amphiphysin 2 (Bin1) and T-Tubule Biogenesis in Muscle" *Science* 297: 1193-6 (2002).
Nicot et al., "Mutations in amphiphysin 2 (BIN1) disrupt interaction with dynamin 2 and cause autosomal recessive centronuclear myopathy" *Nat Genet.* 39(9):1134-9 (2007).
Hong et al. "BIN1 localizes the L-type calcium channel to cardiac T-tubules" *PLoS Biol.* 8(2):e1000312 (2010).
Butler et al. "Amphiphysin II (SH3P9; BIN1), a member of the amphiphysin/Rvs family, is concentrated in the cortical cytomatrix of axon initial segments and nodes of ranvier in brain and around T tubules in skeletal muscle" *J Cell Biol.* 137(6):1355-67 (1997).
Pollack, Andrew, "Doctors Seek New Ways to Treat Loss of Muscle From Aging"—New York Times, Aug. 30, 2010 [retrieved at http://www.nytimes.com/2010/08/31/health/research/31muscle.html . . . ].
Lukaski, Henry, "Sarcopenia: Assessment of Muscle Mass" *J. Nutr.*, 127:994S-997S (1997).
R. Wechsler-Reya, D, Sakamuro, J. Zhang, J. Duhadaway, G. C. Prendergast, *J. Biol. Chem.* 272, 31453 (1997).
Wechsler-Reya. R.J. et al., "A role for the putative tumor suppressor Bin1 1-6,15-16,32-33 in muscle cell differentiation" *Molecular and Cellular Biology*, 18(1): 556-575 (1998).
NCBI GenBank Accession No. NM_004305, Nov. 1, 2000.
Fernando, P. et al., "Bin1 Src Homology 3 domain acts as a scaffold for myofiber sarcomere assembly" Journal of Biological Chemistry, 284(40): 27674-27686 (2009).
International Search Report for PCT/US2011/059574, dated Jun. 20, 2012.

(Continued)

*Primary Examiner* — Amy M Bunker
(74) *Attorney, Agent, or Firm* — Foley & Lardner LLP

(57) ABSTRACT

Provided are methods for determining skeletal muscle mass in subject. Also provided are methods for diagnosing a neurological condition or disease or a condition or disease associated with reduced skeletal muscle mass in a subject. Further provided are purified antibodies that bind specifically to a BIN1 polypeptide that is expressed specifically in skeletal muscle.

20 Claims, 6 Drawing Sheets

(56) References Cited

OTHER PUBLICATIONS

International Preliminary Report on Patentability for PCT/US2011/059574, dated May 23, 2013.
European Application No. 11850406.7, Extended European Search Report, dated Apr. 4, 2014, 11 pages.
Toussaint et al., "Defects in amphiphysin 2 (BIN1) and triads in several forms of centronuclear myopathies", ACTA Neuropathologica, Springer, Berlin, DE, vol. 121, No. 2, Oct. 7, 2010, pp. 253-266.
Chang et al., "BIN1 (bridging integrator 1)", Atlas of Genetics and Cytogenetics in Oncology and Haematology, No. 8, 2009.
European Application No. 11850406.7, Office Action, dated Jan. 23, 2015, 5 pages.
Japanese Patent Application No. 2013-538809, Office Action with English translation, dated Jul. 30, 2015, 7 pages.
European Application No. 11850406.7, Office Action, dated Oct. 12, 2015, 4 pages.
Japanese Patent Application No. 2013-538809, Notice of Allowance with English translation, dated Nov. 30, 2015, 6 pages.
Chang et al., "BIN1 (bridging integrator 1)," Atlas Genet Cytogenet Oncol Haematol., (2009), 13(8):543-548.

* cited by examiner

SEQUENCE LISTING

<160> NUMBER OF SEQ ID NOS: 33

<210> SEQ ID NO 1
<211> LENGTH: 454
<212> TYPE: PRT
<213> ORGANISM: Homo sapiens

<400> SEQUENCE: 1

```
Met Ala Glu Met Gly Ser Lys Gly Val Thr Ala Gly Lys Ile Ala Ser
1               5                   10                  15

Asn Val Gln Lys Lys Leu Thr Arg Ala Gln Glu Lys Val Leu Gln Lys
            20                  25                  30

Leu Gly Lys Ala Asp Glu Thr Lys Asp Glu Gln Phe Glu Gln Cys Val
        35                  40                  45

Gln Asn Phe Asn Lys Gln Leu Thr Glu Gly Thr Arg Leu Gln Lys Asp
    50                  55                  60

Leu Arg Thr Tyr Leu Ala Ser Val Lys Ala Met His Glu Ala Ser Lys
65                  70                  75                  80

Lys Leu Asn Glu Cys Leu Gln Glu Val Tyr Glu Pro Asp Trp Pro Gly
                85                  90                  95

Arg Asp Glu Ala Asn Lys Ile Ala Glu Asn Asn Asp Leu Leu Trp Met
                100                 105                 110

Asp Tyr His Gln Lys Leu Val Asp Gln Ala Leu Leu Thr Met Asp Thr
            115                 120                 125

Tyr Leu Gly Gln Phe Pro Asp Ile Lys Ser Arg Ile Ala Lys Arg Gly
130                 135                 140

Arg Lys Leu Val Asp Tyr Asp Ser Ala Arg His His Tyr Glu Ser Leu
145                 150                 155                 160

Gln Thr Ala Lys Lys Lys Asp Glu Ala Lys Ile Ala Lys Ala Glu Glu
                165                 170                 175

Glu Leu Ile Lys Ala Gln Lys Val Phe Glu Glu Met Asn Val Asp Leu
            180                 185                 190

Gln Glu Glu Leu Pro Ser Leu Trp Asn Ser Arg Val Gly Phe Tyr Val
        195                 200                 205

Asn Thr Phe Gln Ser Ile Ala Gly Leu Glu Glu Asn Phe His Lys Glu
    210                 215                 220

Met Ser Lys Leu Asn Gln Asn Leu Asn Asp Val Leu Val Gly Leu Glu
225                 230                 235                 240

Lys Gln His Gly Ser Asn Thr Phe Thr Val Lys Ala Gln Pro Arg Lys
                245                 250                 255

Lys Ser Lys Leu Phe Ser Arg Leu Arg Arg Lys Lys Asn Ser Asp Asn
            260                 265                 270

Ala Pro Ala Lys Gly Asn Lys Ser Pro Ser Pro Asp Gly Ser Pro
        275                 280                 285

Ala Ala Thr Pro Glu Ile Arg Val Asn His Gly Pro Glu Pro Ala Gly
    290                 295                 300

Gly Ala Thr Pro Gly Ala Thr Leu Pro Lys Ser Pro Ser Gln Pro Ala
305                 310                 315                 320

Glu Ala Ser Glu Val Ala Gly Gly Thr Gln Pro Ala Ala Gly Ala Gln
                325                 330                 335

Glu Pro Gly Glu Thr Ala Ala Ser Glu Ala Ala Ser Ser Ser Leu Pro
            340                 345                 350

Ala Val Val Val Glu Thr Phe Pro Ala Thr Val Asn Gly Thr Val Glu
        355                 360                 365

Gly Gly Ser Gly Ala Gly Arg Leu Asp Leu Pro Pro Gly Phe Met Phe
    370                 375                 380

Lys Val Gln Ala Gln His Asp Tyr Thr Ala Thr Asp Thr Asp Glu Leu
385                 390                 395                 400

Gln Leu Lys Ala Gly Asp Val Val Leu Val Ile Pro Phe Gln Asn Pro
```

```
                    405                 410                 415
Glu Glu Gln Asp Glu Gly Trp Leu Met Gly Val Lys Glu Ser Asp Trp
            420                 425                 430

Asn Gln His Lys Glu Leu Glu Lys Cys Arg Gly Val Phe Pro Glu Asn
            435                 440                 445

Phe Thr Glu Arg Val Pro
        450

<210> SEQ ID NO 2
<211> LENGTH: 16
<212> TYPE: PRT
<213> ORGANISM: Homo sapiens

<400> SEQUENCE: 2

Arg Lys Lys Ser Lys Leu Phe Ser Arg Leu Arg Arg Lys Lys Asn Ser
1               5                   10                  15

<210> SEQ ID NO 3
<211> LENGTH: 2210
<212> TYPE: DNA
<213> ORGANISM: Homo sapiens

<400> SEQUENCE: 3
```

| | | | | | |
|---|---|---|---|---|---|
| cgcgcccctc | cctcctcgcg | gacctggcgg | tgccggcgcc | cggagtggcc | ctttaaaagg | 60 |
| cagcttattg | tccggagggg | gcgggcgggg | ggcgccgacc | gcggcctgag | gcccggcccc | 120 |
| tccctctcc | ctccctctgt | cccgcgtcg | ctcgctggct | agctcgctgg | ctcgctcgcc | 180 |
| cgtccggcgc | acgctccgcc | tccgtcagtt | ggctccgctg | tcgggtgcgc | ggcgtggagc | 240 |
| ggcagccggt | ctggacgcgc | ggccggggct | ggggctggg | agcgcggcgc | gcaagatctc | 300 |
| cccgcgcgag | agcggcccct | gccaccgggc | gaggcctgcg | ccgcgatggc | agagatgggc | 360 |
| agtaaagggg | tgacggcggg | aaagatcgcc | agcaacgtgc | agaagaagct | cacccgcgcg | 420 |
| caggagaagg | ttctccagaa | gctggggaag | gcagatgaga | ccaaggatga | gcagtttgag | 480 |
| cagtgcgtcc | agaatttcaa | caagcagctg | acggagggca | cccggctgca | gaaggatctc | 540 |
| cggacctacc | tggcctccgt | caaagccatg | acgaggctt | ccaagaagct | gaatgagtgt | 600 |
| ctgcaggagg | tgtatgagcc | cgattggccc | ggcagggatg | aggcaaacaa | gatcgcagag | 660 |
| aacaacgacc | tgctgtggat | ggattaccac | cagaagctgg | tggaccaggc | gctgctgacc | 720 |
| atggacacgt | acctgggcca | gttccccgac | atcaagtcac | gcattgccaa | gcgggggcgc | 780 |
| aagctggtgg | actacgacag | tgcccggcac | cactacgagt | cccttcaaac | tgccaaaaag | 840 |
| aaggatgaag | ccaaaattgc | caaggccgag | gaggagctca | tcaaagccca | gaaggtgttt | 900 |
| gaggagatga | atgtggatct | gcaggaggag | ctgccgtccc | tgtggaacag | ccgcgtaggt | 960 |
| ttctacgtca | acacgttcca | gagcatcgcg | ggcctggagg | aaaacttcca | caaggagatg | 1020 |
| agcaagctca | accagaacct | caatgatgtg | ctggtcggcc | tggagaagca | cacgggagc | 1080 |
| aacaccttca | cggtcaaggc | ccagcccaga | aagaaaagta | aactgttttc | gcggctgcgc | 1140 |
| agaaagaaga | acagtgacaa | cgcgcctgca | aagggaaca | agagcccttc | gcctccagat | 1200 |
| ggctcccctg | ccgccacccc | cgagatcaga | gtcaaccacg | agccagagcc | ggccggcggg | 1260 |
| gccacgcccg | ggccaccct | ccccaagtcc | ccatctcagc | cagcagaggc | ctcggaggtg | 1320 |
| gcgggtggga | cccaacctgc | ggctggagcc | caggagccag | gggagacggc | ggcaagtgaa | 1380 |
| gcagcctcca | gctctcttcc | tgctgtcgtg | gtggagacct | tcccagcaac | tgtgaatggc | 1440 |
| accgtggagg | gcggcagtgg | ggccgggcgc | ttggacctgc | ccccaggttt | catgttcaag | 1500 |

```
gtacaggccc agcacgacta cacggccact gacacagacg agctgcagct caaggctggt    1560
gatgtggtgc tggtgatccc cttccagaac cctgaagagc aggatgaagg ctggctcatg    1620
ggcgtgaagg agagcgactg gaaccagcac aaggagctgg agaagtgccg tggcgtcttc    1680
cccgagaact tcactgagag ggtccccatga cggcggggcc caggcagcct ccgggcgtgt    1740
gaagaacacc tcctcccgaa aaatgtgtgg ttcttttttt tgttttgttt tcgttttttca    1800 tcttttgaag agcaaaggga aatcaagagg agacccccag gcagaggggc gttctcccaa    1860
agattaggtc gttttccaaa gagccgcgtc ccggcaagtc cggcggaatt caccagtgtt    1920
cctgaagctg ctgtgtcctc tagttgagtt tctggcgccc ctgcctgtgc cgcatgtgt    1980 gcctggccgc agggcggggc tggggctgc cgagccacca tgcttgcctg aagcttcggc    2040
cgcgccaccc gggcaagggt cctcttttcc tggcagctgc tgtgggtggg gcccagacac    2100
cagcctagcc tggctctgcc ccgcagacgg tctgtgtgct gtttgaaaat aaatcttagt    2160
gttcaaaaca aaatgaaaca aaaaaaaaat gataaaaact ctcaaaaaaa              2210

<210> SEQ ID NO 4
<211> LENGTH: 322
<212> TYPE: DNA
<213> ORGANISM: Unknown
<220> FEATURE:
<223> OTHER INFORMATION: Synthetic Construct

<400> SEQUENCE: 4
gacattgtga tgacccagtc tcacaaattc atgtccacat cagtaggaga cagggtcagc      60
atcacctgca aggccagtca ggatgtgagt actgctgtag cctggtatca acagaaacca     120
ggacaatctc ctaaaactact gatttactcg gcatcctacc ggtacactgg agtccctgat     180
cgcttcactg gcagtggatc tgggacggat ttcactttca ccatcagcag tgtgcaggct     240
gaagacctgg cagtttatta ctgtcagcaa cattatagta ctccgctcac gttcggtgct     300
gggaccaagc tggagctgaa ac                                             322

<210> SEQ ID NO 5
<211> LENGTH: 107
<212> TYPE: PRT
<213> ORGANISM: Unknown
<220> FEATURE:
<223> OTHER INFORMATION: Synthetic Construct

<400> SEQUENCE: 5

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Leu
                85                  90                  95

Thr Phe Gly Ala Gly Thr Lys Leu Glu Leu Lys
            100                 105
```

<210> SEQ ID NO 6
<211> LENGTH: 359
<212> TYPE: DNA
<213> ORGANISM: Unknown
<220> FEATURE:
<223> OTHER INFORMATION: Synthetic Construct

<400> SEQUENCE: 6

```
caggtccagc tgcagcagtc tggacctgag ctggtgaagc ctggggcttc agtgaggata      60
tcctgcaagg cttctgggta caccttcaca aggtactata tacactggtt gaagcagagg     120
cctggacagg gacctgagtg gattggatgg atttatcctg gaaatgttaa tactaagtac     180
aatgagaagt tcaagggcaa ggccacactg actgcagaca atcctccag cacagcctac      240
atgcagctca gcagcctgac ctctgaggac tctgcggtct atttctgtgc aagagagggg     300
tcctatgaat acgacgaggc tgactactgg ggcccaggca ccaccctcac agtctcctc     359
```

<210> SEQ ID NO 7
<211> LENGTH: 120
<212> TYPE: PRT
<213> ORGANISM: Unknown
<220> FEATURE:
<223> OTHER INFORMATION: Synthetic Construct

<400> SEQUENCE: 7

```
Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Arg Tyr
            20                  25                  30

Tyr Ile His Trp Leu Lys Gln Arg Pro Gly Gln Gly Pro Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Gly Ser Tyr Glu Tyr Asp Glu Ala Asp Tyr Trp Gly Pro
            100                 105                 110

Gly Thr Thr Leu Thr Val Ser Ser
        115                 120
```

<210> SEQ ID NO 8
<211> LENGTH: 6
<212> TYPE: PRT
<213> ORGANISM: Unknown
<220> FEATURE:
<223> OTHER INFORMATION: Synthetic Construct

<400> SEQUENCE: 8

```
Gln Asp Val Ser Thr Ala
1               5
```

<210> SEQ ID NO 9
<211> LENGTH: 4
<212> TYPE: PRT
<213> ORGANISM: Unknown
<220> FEATURE:
<223> OTHER INFORMATION: Synthetic Construct

<400> SEQUENCE: 9

Ser Ala Ser Tyr

<210> SEQ ID NO 10
<211> LENGTH: 9
<212> TYPE: PRT
<213> ORGANISM: Unknown
<220> FEATURE:
<223> OTHER INFORMATION: Synthetic Construct

<400> SEQUENCE: 10

Gln Gln His Tyr Ser Thr Pro Leu Thr
1               5

<210> SEQ ID NO 11
<211> LENGTH: 8
<212> TYPE: PRT
<213> ORGANISM: Unknown
<220> FEATURE:
<223> OTHER INFORMATION: Synthetic Construct

<400> SEQUENCE: 11

Gly Tyr Thr Phe Thr Arg Tyr Tyr
1               5

<210> SEQ ID NO 12
<211> LENGTH: 8
<212> TYPE: PRT
<213> ORGANISM: Unknown
<220> FEATURE:
<223> OTHER INFORMATION: Synthetic Construct

<400> SEQUENCE: 12

Ile Tyr Pro Gly Asn Val Asn Thr
1               5

<210> SEQ ID NO 13
<211> LENGTH: 13
<212> TYPE: PRT
<213> ORGANISM: Unknown
<220> FEATURE:
<223> OTHER INFORMATION: Synthetic Construct

<400> SEQUENCE: 13

Ala Arg Glu Gly Ser Tyr Glu Tyr Asp Glu Ala Asp Tyr
1               5                   10

<210> SEQ ID NO 14
<211> LENGTH: 322
<212> TYPE: DNA
<213> ORGANISM: Unknown
<220> FEATURE:
<223> OTHER INFORMATION: Synthetic Construct

<400> SEQUENCE: 14
gacattgtga tgacccagtc tcacaaattc atgtccacat cagtaggaga cagggtcagc      60
atcacctgca aggccagtca ggatgtgagt actgctgtag cctggtatca acagaaacca     120
ggacaatctc ctaaactact gatttactcg gcatcctacc ggtacactgg agtccctgat     180
cgcttcactg gcagtggatc tgggacggat ttcactttca ccatcagcag tgtgcaggct     240
gaagacctgg cagtttatta ctgtcagcaa cattatagta ctccgctcac gttcggtgct     300
gggaccaagc tggagctgaa ac                                              322

<210> SEQ ID NO 15
<211> LENGTH: 107

```
<212> TYPE: PRT
<213> ORGANISM: Unknown
<220> FEATURE:
<223> OTHER INFORMATION: Synthetic Construct

<400> SEQUENCE: 15

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Leu
                85                  90                  95

Thr Phe Gly Ala Gly Thr Lys Leu Glu Leu Lys
            100                 105

<210> SEQ ID NO 16
<211> LENGTH: 359
<212> TYPE: DNA
<213> ORGANISM: Unknown
<220> FEATURE:
<223> OTHER INFORMATION: Synthetic Construct

<400> SEQUENCE: 16
caggtccagc tgcagcagtc tggacctgag ctggtgaagc ctggggcttc agtgaggata      60
tcctgcaagg cttctgggta caccttcaca aggtactata tacactggtt gaagcagagg     120
cctggacagg gacctgagtg gattggatgg atttatcctg gaaatgttaa tactaagtac     180
aatgagaagt tcaagggcaa ggccacactg actgcagaca atcctccag cacagcctac      240 atgcagctca gcagcctgac ctctgaggac tctgcggtct atttctgtgc aagagagggg     300
tcctatgaat acgacgaggc tggctactgg ggcccaggca ccaccctcac agtctcctc     359

<210> SEQ ID NO 17
<211> LENGTH: 120
<212> TYPE: PRT
<213> ORGANISM: Unknown
<220> FEATURE:
<223> OTHER INFORMATION: Synthetic Construct

<400> SEQUENCE: 17

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Arg Tyr
            20                  25                  30

Tyr Ile His Trp Leu Lys Gln Arg Pro Gly Gln Gly Pro Glu Trp Ile
        35                  40                  45

Gly Trp Ile Tyr Pro Gly Asn Val Asn Thr Lys Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Gly Ser Tyr Glu Tyr Asp Glu Ala Gly Tyr Trp Gly Pro
```

-continued

```
              100                 105                 110

Gly Thr Thr Leu Thr Val Ser Ser
        115                 120

<210> SEQ ID NO 18
<211> LENGTH: 6
<212> TYPE: PRT
<213> ORGANISM: Unknown
<220> FEATURE:
<223> OTHER INFORMATION: Synthetic Construct

<400> SEQUENCE: 18

Gln Asp Val Ser Thr Ala
1               5

<210> SEQ ID NO 19
<211> LENGTH: 4
<212> TYPE: PRT
<213> ORGANISM: Unknown
<220> FEATURE:
<223> OTHER INFORMATION: Synthetic Construct

<400> SEQUENCE: 19

Ser Ala Ser Tyr
1

<210> SEQ ID NO 20
<211> LENGTH: 9
<212> TYPE: PRT
<213> ORGANISM: Unknown
<220> FEATURE:
<223> OTHER INFORMATION: Synthetic Construct

<400> SEQUENCE: 20

Gln Gln His Tyr Ser Thr Pro Leu Thr
1               5

<210> SEQ ID NO 21
<211> LENGTH: 8
<212> TYPE: PRT
<213> ORGANISM: Unknown
<220> FEATURE:
<223> OTHER INFORMATION: Synthetic Construct

<400> SEQUENCE: 21

Gly Tyr Thr Phe Thr Arg Tyr Tyr
1               5

<210> SEQ ID NO 22
<211> LENGTH: 8
<212> TYPE: PRT
<213> ORGANISM: Unknown
<220> FEATURE:
<223> OTHER INFORMATION: Synthetic Construct

<400> SEQUENCE: 22

Ile Tyr Pro Gly Asn Val Asn Thr
1               5

<210> SEQ ID NO 23
<211> LENGTH: 13
<212> TYPE: PRT
<213> ORGANISM: Unknown
<220> FEATURE:
<223> OTHER INFORMATION: Synthetic Construct

<400> SEQUENCE: 23
```

Ala Arg Glu Gly Ser Tyr Glu Tyr Asp Glu Ala Gly Tyr
1               5                   10

<210> SEQ ID NO 24
<211> LENGTH: 338
<212> TYPE: DNA
<213> ORGANISM: Unknown
<220> FEATURE:
<223> OTHER INFORMATION: Synthetic Construct

<400> SEQUENCE: 24
gatgttgtga tgacccagac tccactcact ttgtcggtta ccattggaca accagcctcc      60
atctcttgca agtcaagtca gagcctctta gatagtgatg gaaagacata tttgaattgg     120
ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttccg     300
tacacgttcg agggggggac caagctggaa ataaaacg                             338

<210> SEQ ID NO 25
<211> LENGTH: 113
<212> TYPE: PRT
<213> ORGANISM: Unknown
<220> FEATURE:
<223> OTHER INFORMATION: Synthetic Construct

<400> SEQUENCE: 25

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg

<210> SEQ ID NO 26
<211> LENGTH: 333
<212> TYPE: DNA
<213> ORGANISM: Unknown
<220> FEATURE:
<223> OTHER INFORMATION: Synthetic Construct

<400> SEQUENCE: 26
gaggttcagc tgcagcagtc tggggcagag cttgtgaggt caggggcctc agtcaagttg      60
tcctgcacag cttctggctt caacattaaa gactactata tgcactgggt gaagcagagg     120
cctgaacagg gcctggagtg gattggatgg attgatcctg agaatggtga tactgaatat     180
gccccgaagt tccagggcaa ggccactgtg actgcagaca catcctccaa cacagcctac     240
ctgcagctca gcagcctgac atctgaggac actgccgtct attactgtaa ctctgactac     300
tggggccaag gcaccactct cacagtctcc tca                                        333

<210> SEQ ID NO 27
<211> LENGTH: 111
<212> TYPE: PRT
<213> ORGANISM: Unknown
<220> FEATURE:
<223> OTHER INFORMATION: Synthetic Construct

<400> SEQUENCE: 27

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Val Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Ser Asp Tyr Trp Gly Gln Gly Thr Thr Leu Thr Val Ser Ser
            100                 105                 110

<210> SEQ ID NO 28
<211> LENGTH: 11
<212> TYPE: PRT
<213> ORGANISM: Unknown
<220> FEATURE:
<223> OTHER INFORMATION: Synthetic Construct

<400> SEQUENCE: 28

Gln Ser Leu Leu Asp Ser Asp Gly Lys Thr Tyr
1               5                   10

<210> SEQ ID NO 29
<211> LENGTH: 4
<212> TYPE: PRT
<213> ORGANISM: Unknown
<220> FEATURE:
<223> OTHER INFORMATION: Synthetic Construct

<400> SEQUENCE: 29

Leu Val Ser Lys
1

<210> SEQ ID NO 30
<211> LENGTH: 9
<212> TYPE: PRT
<213> ORGANISM: Unknown
<220> FEATURE:
<223> OTHER INFORMATION: Synthetic Construct

<400> SEQUENCE: 30

Trp Gln Gly Thr His Phe Pro Tyr Thr
1               5

<210> SEQ ID NO 31
<211> LENGTH: 8
<212> TYPE: PRT
<213> ORGANISM: Unknown
<220> FEATURE:
<223> OTHER INFORMATION: Synthetic Construct -continued

```
<400> SEQUENCE: 31

Gly Phe Asn Ile Lys Asp Tyr Tyr
1               5

<210> SEQ ID NO 32
<211> LENGTH: 8
<212> TYPE: PRT
<213> ORGANISM: Unknown
<220> FEATURE:
<223> OTHER INFORMATION: Synthetic Construct

<400> SEQUENCE: 32

Ile Asp Pro Glu Asn Gly Asp Thr
1               5

<210> SEQ ID NO 33
<211> LENGTH: 4
<212> TYPE: PRT
<213> ORGANISM: Unknown
<220> FEATURE:
<223> OTHER INFORMATION: Synthetic Construct

<400> SEQUENCE: 33

Asn Ser Asp Tyr
1
```

BIN1 EXPRESSION AS A MARKER OF SKELETAL MUSCLE MASS AND NEUROLOGICAL CONDITIONS

CROSS REFERENCE TO RELATED APPLICATION

This application claims the benefit of U.S. Provisional Application No. 61/411,683, filed on Nov. 9, 2010, which is incorporated by reference herein in its entirety.

BACKGROUND

Skeletal muscle is the largest organ in the body and there is increasing awareness of the importance of skeletal muscle in biological function. Skeletal muscle loss afflicts a large number of individuals causing a range of dysfunction and disability. For example, sarcopenia affects about ten percent of individuals over sixty years of age, with higher rates as age advances. Other conditions such as, for example, multiple sclerosis or chronic disease, can also lead to reduced muscle mass.

SUMMARY

Provided are methods for determining skeletal muscle mass in a subject. The methods comprise detecting a level of BIN1 expression in a biological sample from the subject and comparing the detected level of BIN1 expression to a control level of BIN1 expression. The level of BIN1 expression relative to the control level indicates the skeletal muscle mass of the subject.

Also provided are methods for diagnosing a condition or disease associated with reduced or increased skeletal muscle mass in a subject. The methods comprise detecting a level of BIN1 expression in a biological sample from the subject and comparing the detected level of BIN1 expression to a control level of BIN1 expression. The level of BIN1 expression relative to the control level indicates that the subject has a disease or condition associated with reduced or increased skeletal muscle mass as compared to control.

Also provided are methods for diagnosing a neurological condition or disease. The methods comprise detecting a level of BIN1 expression in a biological sample from the subject and comparing the detected level of BIN1 expression to a control level of BIN1 expression. The level of BIN1 expression relative to the control level indicates that the subject has a neurological disease or condition.

Further provided are purified antibodies that bind specifically to a BIN1 polypeptide that is expressed specifically in skeletal muscle.

The details of one or more embodiments are set forth in the accompanying drawings and the description below. Other features, objects, and advantages will be apparent from the description and drawings, and from the claims.

DESCRIPTION OF DRAWINGS

FIG. 5 is a scatter plot of canine muscle weight (in kg, calculated by fraction of live weight and adjusted for MM) versus measured skBIN1 levels (A.U.) quantified from the plasma fraction of venous blood samples. A line fit by linear regression has a slope of 0.8. *P<0.05, n=34.

FIG. 6 is a scatter plot of bovine muscle weight (in kg, calculated by dressed (warm) weight less 20% to account for bone) versus measured skBIN1 levels (A.U.) quantified from the plasma fraction of venous blood samples. A line fit by linear regression has a slope of 0.2 with *P<0.05, n=25.

FIG. 7 shows a bar graph of mean measured skBIN1 levels (A.U.) against animal type (left graph) and mean determined muscle weight against animal type (right graph). Relative ratios of cow to dog are similar whether parameter measured as skBIN1 or net muscle weight. Values expressed as mean±standard deviation.

DETAILED DESCRIPTION

Figure 1:
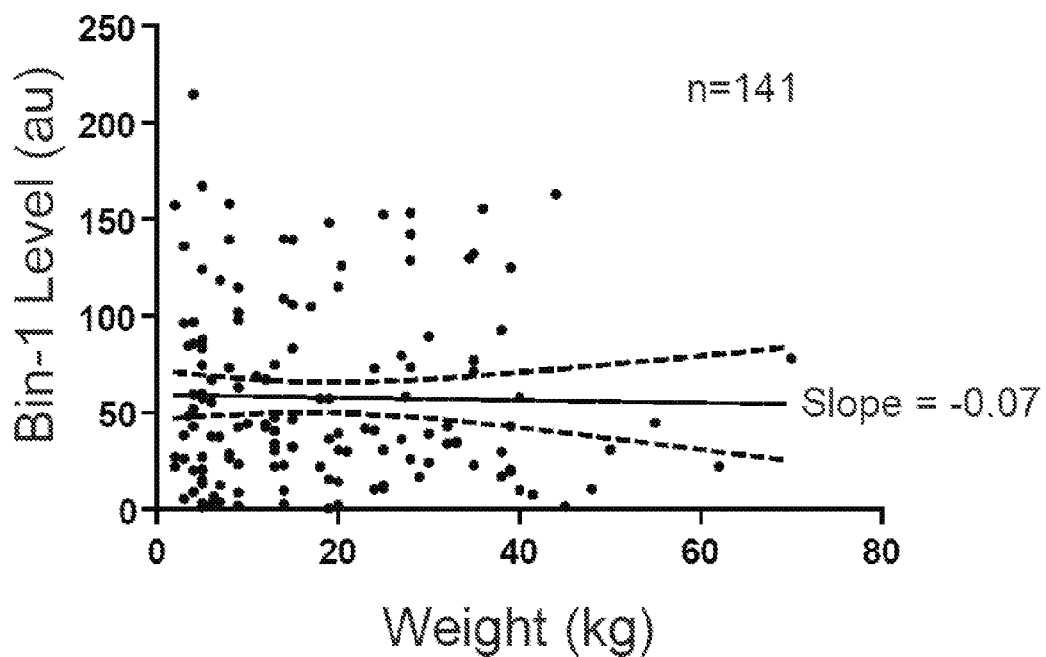
FIG. 1 is a scatter plot of measured BIN1 levels (A.U.) versus measured weight (kilograms (kg)) in canine subjects. A line fit by linear regression has a slope of −0.07 indicating there is little dependency of BIN1 on weight across all breeds of dogs.

Methods described herein are based on the finding that muscle mass in a subject can be directly correlated to levels of BIN1 expression in the subject. For example, a decrease in BIN1 expression correlates with a decrease in skeletal muscle mass of the subject when compared to a control. Accordingly, BIN1 expression can be used as a marker to determine the skeletal muscle mass of a subject.

The bridging integrator 1 (BIN1) gene encodes a nucleo-cytosolic protein which was initially identified as a Myc-interacting protein with features of a tumor suppressor. BIN1 is also known as amphiphysin II, amphiphysin-like, and box dependant MYC interacting protein 1. Alternate splicing of the BIN1 gene results in ten transcript variants encoding different isoforms. Some isoforms of BIN1 are expressed ubiquitously while others show a tissue specific expression. BIN1 isoforms 1-7 are expressed in neurons. Isoform 8 is skeletal muscle specific, while isoforms 9 and 10 are ubiquitous. Isoforms that are expressed in the central nervous system may be involved in synaptic vesicle endocytosis and may interact with dynanim, synaptojanin, endophilin, and clathrin. Aberrant splice variants expressed in tumor cell lines have also been described. A skeletal muscle specific BIN1 is a BIN1 that is expressed exclusively in skeletal muscle or that is predominantly expressed in the skeletal muscle as compared to other tissues.

Provided herein are methods for determining skeletal muscle mass in a subject. A subject can be a vertebrate, and more specifically a mammal (e.g., a human, horse, pig, rabbit, dog, sheep, goat, non-human primate, cow, cat, guinea pig or rodent), a fish, a bird or a reptile or an amphibian. The term does not denote a particular age or sex. Thus, adult and newborn subjects, as well as fetuses, whether male or female, are intended to be covered. As used herein, patient or subject may be used interchangeably and can refer to a subject with or at risk of developing a disease or disorder. The term patient or subject includes human and veterinary subjects.

The methods comprise detecting a level of BIN1 expression in a biological sample from the subject and comparing the detected level of BIN1 expression to a control level of BIN1 expression. The level of BIN1 expression relative to the control level can be used to indicate skeletal muscle mass in the subject. For example, a detected level that is lower than a control level (from the same subject, e.g., prior to the onset or in the absence of a parameter such as disease or inactivity; from a control subject; or a known control value based on a pool of control subjects) indicates decreased skeletal muscle mass in the subject. Moreover, a detected level that is higher than a control level indicates increased skeletal muscle mass in the subject.

As used herein, control level refers to a level of BIN1 expression from the same subject or a different subject or subjects. A level of BIN1 expression from the same subject can be obtained at various time points previous to the most recent time point for comparison as to the levels of BIN1 expression. A level of BIN1 expression from a different subject can be obtained at the same time point as the present subject (e.g., the control subject and the present subject are the same age). Generally, the control subject and the present subject share many of the same or similar characteristics (e.g., age, weight, height, ethnicity, and breed).

A biological sample can be any sample obtained from an organism. Examples of biological samples include body fluids and tissue specimens. The source of the sample may be physiological media as blood, serum, plasma, skeletal muscle tissue, cerebral spinal fluid, breast milk, pus, tissue scrapings, washings, urine, feces, tissue, such as lymph nodes, spleen or the like. The term tissue refers to any tissue of the body, including blood, connective tissue, epithelium, contractile tissue (including skeletal muscle), neural tissue, and the like.

A control level may be obtained from a control sample, which can comprise either a sample obtained from a control subject (e.g., from the same subject at a different time than the biological sample), or from a second subject, or can comprise a known standard. Optionally, the control level is taken from an individual of a population having expected or standard muscle mass for an individual of that population. For example, for male humans, the control level may be the level of BIN1 expression obtained from a twenty-five year old male having a medium muscular build and a body mass index (BMI) of 22 to 23 kg/m$^2$. For female humans, the control level may be the level of BIN1 expression obtained from a twenty-five year old female having a medium muscular build and a body mass index (BMI) of 22 to 23 kg/m$^2$.

Optionally, the biological sample is blood or plasma. Optionally, the biological sample is skeletal muscle tissue (e.g., a muscle biopsy). The BIN1 detected in blood, plasma or skeletal muscle tissue can be a skeletal muscle specific BIN1.

The control level can be normal. In such case, a detected level less than the control level indicates diminished skeletal muscle mass in the subject, whereas, a detected level higher than the control indicates increased muscle mass in the subject. Optionally, the control level is lower than normal, and a detected level comparable to or less than the control level indicates diminished skeletal muscle mass in the subject. Optionally, the control level is higher than normal, and a detected level comparable to or higher than the control level indicates increased skeletal muscle mass in the subject.

Also provided herein are methods for diagnosing and/or monitoring a condition or disease associated with reduced skeletal muscle mass in a subject. Monitoring includes the determination as to whether a disease or condition has improved, worsened or remained unchanged. The disease or condition can be selected from the group consisting of multiple sclerosis, atrophy, neurogenic atrophy, a chronic inflammatory condition, and sarcopenia. If monitoring detects a change, then treatment is optionally modified. For example, if reduction in muscle mass is detected, a regime of physical therapy initiated or increased.

The disease or condition can optionally be another disease or condition associated with muscle atrophy, which can include, but is not limited to muscle injury, prolonged bed rest or inactivity, prolonged immobility, nerve injury, neuropathy, diabetic neuropathy, alcoholic neuropathy, subacute combined degeneration of the spinal cord, diabetes, rheumatoid arthritis, motor neuron diseases, muscular dystrophy (e.g., Duchenne, Becker's, fascioscapulohumeral, limb girdle oculopharyngeal dystrophy, myotonic dystrophy), carpal tunnel syndrome, chronic infection, tuberculosis, muscle and joint disuse, arthritis, joint injuries, joint inflammation, paralysis of limbs, nerve entrapment, damage to nerve supplying muscle, spinal cord lesion, primary muscle disease (myopathy), malnutrition, alcoholism, drug use (e.g., cocaine), medications (e.g., statins, penicillamine), anorexia nervosa, malignancy, chronic disease, viral infections (e.g., HIV, coxsacki B virus), glandular fever, bacterial infections (e.g., tuberculosis), parasitic infections (e.g., schistosomiasis), endocrine disorders (e.g., thyroid disease, Addison's disease, Cushing's disease), herniated disk, hypercortisolism, burns, amyotrophic lateral sclerosis (ALS), spinal cord injury, protein deficiency, radiculopathy, thyrotoxicosis, peripheral nerve trauma, osteoarthritis, Parkinson's disease, multiple sclerosis, prolonged steroid therapy, cerebrovascular accident, peripheral neuropathy, malaria, hookworm infestation, chronic diarrhea, old age, disuse of limb, immobilized fractures, vascular disease, thrombosis of great vessel, embolism of great vessel, ischemia of motor nerves, Buerger's disease, polyarteritis nodosa, ischemic palsy, Volkmann's contracture, soft tissue edema, soft tissue hemorrhage, polio, syringomyelia, haematomyelia, intramedullary tumor, syphilitic amyotrophy, herpes zoster, athermoatous disease, meningovascular malformations, spinal cord tumor, lumbar spondylosis, lumbar canal stenosis, spinal tumor, prolapsed lumbar intervertebral disc, cervical spondylosis, polymyositis, dermatomyositis, trichinosis, toxoplasmosis, glycogen storage myopathy, carnitine deficiency, adrenal dysfunction, meniscal tear, Creutzfeldt-Jakob disease, sarcoidosis, steroid use.

The methods for diagnosing a condition or disease associated with reduced skeletal muscle mass comprise detecting a level of BIN1 expression in a biological sample from the subject and comparing the detected level of BIN1 expression to a control level of BIN1 expression. The level of BIN1 expression relative to the control level indicates the subject has a disease or condition associated with reduced skeletal muscle mass. A detected level that is lower than a control level from the subject indicates that the subject has a disease or condition associated with reduced skeletal muscle mass. Optionally, the control level is a normal level of BIN1 in a selected biological sample, and a detected level less than the control level is used to indicate that the subject has a disease or condition associated with reduced skeletal muscle mass. A detected level may be taken from the same tissue type as the control level. For example, if the control level is from blood, the detected level for comparison to the control level may be from blood. Optionally, the control level is lower than normal, and a detected level comparable to or less than the control level indicates that the subject has a disease or condition associated with reduced skeletal muscle mass. Optionally, the methods further comprise selecting a subject having or suspected of having a disease or condition associated with reduced skeletal muscle mass.

Also provided herein are methods for diagnosing a condition or disease associated with increased skeletal muscle mass in a subject. The methods comprise detecting a level of BIN1 expression in a biological sample from the subject and comparing the detected level of BIN1 expression to a control level of BIN1 expression. The level of BIN1 expression relative to the control level indicates the subject has a disease or condition associate with increased skeletal muscle mass. Optionally, the method further comprises selecting a subject having or suspected of having a disease or condition associated with increased muscle mass. The disease or condition can be selected from the group consisting of strength training, anabolic steroid use, hypothyroidism, and myotonia dystrophy syndromes.

Also provided are methods for diagnosing a neurological condition or disease. The methods comprise detecting a level of BIN1 expression in a biological sample from the subject and comparing the detected level of BIN1 expression to a control level of BIN1 expression. The level of BIN1 expression relative to the control level indicates that the subject has a neurological disease or condition. Optionally, the biological sample comprises cerebrospinal fluid. A detected level that is lower than a control level indicates the subject has a neurological condition or disease. Optionally, the control level is a normal level of BIN1, and a detected level less than the control level is used to indicate that the subject has a neurological condition or disease. Optionally, the control level is lower than normal and a detected level comparable to or less than the control level indicates that the subject has a neurological condition or disease. Optionally, the methods further comprise selecting a subject having or suspected of having a neurological condition or disease.

Neurological disease and conditions include diseases and conditions associated with neuron loss or dysfunction. Neurological diseases and conditions include, for example, Alzheimer's disease, stroke, spinal cord injury, traumatic brain injury, depression, dementia, multiple sclerosis, Parkinson's disease, depression, Huntington's Disease, ALS and psychosis.

A control level may be obtained from a control sample, which can comprise either a sample obtained from a control subject (e.g., from the same subject at a different time than the biological sample), or from a second subject, or can comprise a known standard. Optionally, the control level is taken from an individual of a population having no signs of a neurological condition or disease for an individual of that population. For example, the control level may be the level of BIN1 expression obtained from a twenty-five year old male or female having no particular signs or symptoms of a neurological condition or disease.

As described throughout, the methods can be practiced on both human and non-human subjects. For example, a level of BIN1 expression can be used to diagnose and/or monitor the diseases and conditions listed above in non-human animals. Optionally, BIN1 expression level is used to diagnose or monitor conditions associated with atrophy (e.g. reduced BIN1 levels) or hypertrophy (e.g. increased BIN1 levels) in canine, feline and equine subjects. Moreover, BIN1 expression levels can be used to assess muscle mass to objectively determine production stages, to grade muscle development, and/or to improve genetic lines in production animals, such as, for example, avian, bovine, caprine, ovine, and porcine subjects and populations thereof.

For example, BIN1 expression levels can be determined in a production animal subject, or a population (e.g., two or more production animals) of production animal subjects. A detected level of BIN1 as compared to a control level of BIN1 can indicate increased muscle mass in the subject or population of subjects. For example, individual animals or populations with increased BIN1 expression levels can be optionally selected for breeding programs to improve genetic stock for higher muscle mass.

In other examples, BIN1 expression levels can be used to assess muscle mass development in performance animals including, for example, canines and equines. A detected level of BIN1 as compared to a control BIN1 level can indicate increased muscle mass in a performance animal, such as a race horse or dog. Increased muscle mass may indicate the effect of training, nutritional or other factors used to enhance performance of the animal. Optionally, a detected level of BIN1 as compared to a control BIN1 level indicates decreased muscle mass in a performance animal, such as a race horse or dog. Decreased muscle mass may also indicate the effect of training, nutritional or other factors used to enhance performance of the animal. Therefore an individual, such as a trainer or breeder, can use BIN1 levels to guide management decisions related to the animal's performance. Moreover, as with the production animals, individual performance animals or populations with desired levels of BIN1, for example increased BIN1 expression levels, can be optionally selected for breeding programs to improve genetic stock to better achieve desired levels of muscle mass, such as increased muscle mass.

In the described methods, the BIN1 can be a BIN1 that is expressed specifically in skeletal muscle. As described above, a skeletal muscle specific BIN1 is a BIN1 that is expressed exclusively in skeletal muscle or that is predominantly expressed in skeletal muscle as compared to other tissues. The BIN1 can, for example, be a skeletal muscle specific BIN1 isoform. Optionally, the skeletal muscle specific BIN1 isoform is BIN1 isoform 8. Optionally, the skeletal muscle specific BIN1 isoform comprises SEQ ID NO:1. Optionally, the skeletal muscle specific isoform comprises SEQ ID NO:2.

The level of BIN1 expression can, for example, be determined by detecting BIN1 polypeptide in the biological sample. Optionally, the level of BIN1 expression can be determined by detecting a BIN1-encoding nucleic acid (e.g., BIN1 mRNA), or fragment thereof, in the biological sample. Examples of analytical techniques useful in determining the expression of BIN1 include reverse transcription-polymerase chain reaction (RT-PCR), quantitative real time-PCR (qRT-PCR), one step PCR, RNase protection assay, primer extension assay, microarray analysis, gene chip, in situ hybridization, immunohistochemistry, Northern blot, Western blot, enzyme-linked immunosorbent assay (ELISA), enzyme immunoassay (EIA), radioimmunoassay (RIA), or protein array. These techniques are known. See, e.g., Sambrook et al., Molecular Cloning: A Laboratory Manual, 3$^{rd}$ Ed., Cold Spring Harbor Press, Cold Spring Harbor, N.Y. (2001).

When RT-PCR is used to determine BIN1 expression, mRNA can be isolated from a biological sample. Optionally, RNA is isolated from blood, plasma or skeletal muscle tissue of a subject, and optionally, from corresponding normal tissue or subject as a control.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andrés et al., BioTechniques 18:42044 (1995). Optionally, RNA isolation can be performed using a purification kit, buffer set and protease from commercial manufacturers according to the manufacturer's instructions. For example, total RNA can be isolated using Qiagen RNeasy® mini-columns (Hilden, Del.). Other commercially available RNA isolation kits include MasterPure® Complete DNA and RNA Purification Kit (EPICENTRE®, Madison, Wis.), and Paraffin Block RNA Isolation Kit® (Ambion, Inc., Austin, Tex.). Total RNA from tissue samples can be isolated using RNA Stat-60® (Tel-Test, Friendswood, Tex.). RNA prepared from a biological sample can be isolated, for example, by cesium chloride density gradient centrifugation.

The RNA template can be transcribed into cDNA, followed by its exponential amplification in a PCR reaction. A number of reverse transcriptases may be used, including, but not limited to, Avian Myeloblastosis Virus Reverse Transcriptase (AMV-RT), Moloney Murine Leukemia Virus Reverse Transcriptase (MMLV-RT), reverse transcriptase from human T-cell leukemia virus type I (HTLV-I), bovine leukemia virus (BLV), Rous sarcoma virus (RSV), human immunodeficiency virus (HIV) and *Thermus thermophilus* (Tth). The reverse transcription step is typically primed using specific primers, random hexamers, or oligo-dT primers, depending on the circumstances and the goal of RT-PCR. For example, extracted RNA can be reverse-transcribed using a GeneAmp RNA PCR kit (Perkin Elmer, Waltham, Mass.), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme and is labeled with a reporter fluorescent dye and a quencher fluorescent dye. Any laser-induced emission from the reporter dye is quenched by the quenching dye when the two dyes are located close together as they are on the probe.

During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

RT-PCR can be performed using commercially available equipment, such as, for example, ABI PRISM 7700™ Sequence Detection System® (Perkin-Elmer-Applied Biosystems, Foster City, Calif.), or Lightcycler® (Roche Molecular Biochemicals, Mannheim, Del.). Optionally, the 5' nuclease procedure is run on a real-time quantitative PCR device. Such a system can comprise a thermocycler, laser, charge-coupled device (CCD), camera and computer. The system amplifies samples in a 96-well format on a thermocycler. During amplification, laser-induced fluorescent signal is collected in real-time through fiber optic cables for all 96 wells, and detected at the CCD. The system includes software for running the instrument and for analyzing the data.

5'-Nuclease assay data are initially expressed as Ct, or the threshold cycle. Fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is optionally performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A variation of the RT-PCR technique is the real time quantitative PCR, which measures PCR product accumulation through a dual-labeled fluorogenic probe. Real time PCR is compatible both with quantitative competitive PCR, where internal competitor for each target sequence is used for normalization, and with quantitative comparative PCR using a normalization gene contained within the sample, or a housekeeping gene for RT-PCR.

To correct for (normalize away) both differences in the amount of RNA assayed and variability in the quality of the RNA used the assay can optionally incorporate analysis of the expression of certain reference genes (or "normalizing genes"), including well known housekeeping genes, such as GAPDH, HPRT1, ubiquitin, etc.

Alternatively, normalization can be based on the mean or median signal (Ct) of all of the assayed genes or a large subset thereof (often referred to as a "global normalization" approach). On a gene-by-gene basis, measured normalized amount of a subject tissue mRNA may be compared to the amount found in a corresponding normal tissue.

For example, primers and probes (e.g., for use in PCR amplification-based methods) can be designed based upon exon sequence to be amplified. Accordingly, the primer/probe design can include determining a target exon sequence within the gene of interest. This can be done by publicly available software, such as the DNA BLAST software developed by Kent, W. J., Genome Res. 12(4):656-64 (2002), or by the BLAST software including its variations. One target exon sequence that can be used is SEQ ID NO:2. Subsequent steps follow well established methods of PCR primer and probe design.

In order to avoid non-specific signals, repetitive sequences within the target sequence of the gene can be optionally masked when designing the primers and probes. The masked sequences can then be used to design primer and probe sequences using any commercially or otherwise publicly available primer/probe design packages, such as Primer Express (Applied Biosystems, Carlsbad, Calif.); MGB assay-by-design (Applied Biosystems, Carlsbad, Calif.).

Factors to be considered in PCR primer design can include primer length, melting temperature (Tm), G/C content, specificity, complementary primer sequences, and 3'-end sequence. PCR primers can optionally be 17-30 bases in length, and contain about 20-80% G+C bases, (e.g., about 50-60% G+C bases). Tm's between 50° C. and 80° C., e.g. about 50° C. to 70° C.

Microarray technology may be used to detect differential expression of BIN1 in a subject's biological sample and normal or control biological sample. In this method, polynucleotide sequences of interest (including cDNAs and oligonucleotides) are plated, or arrayed, on a microchip substrate. The arrayed sequences are then hybridized with specific DNA probes from cells or tissues of interest. Similar to the RT-PCR method, the source of mRNA is optionally total RNA isolated from subject's biological sample, and optionally corresponding normal or control biological sample.

Fluorescently labeled cDNA probes can be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element can be used for assessment of corresponding mRNA abundance.

With dual color fluorescence, separately labeled cDNA probes generated from two sources of RNA are hybridized pair wise to the array. The relative abundance of the transcripts from the two sources corresponding to each specified gene is thus determined simultaneously. Microarray methods have been shown to have the sensitivity to detect rare transcripts, which are expressed at a few copies per cell, and to reproducibly detect at least approximately two-fold differences in the expression levels (Schena et al., Proc. Natl. Acad. Sci. USA 93(2):106-149 (1996)).

The arrayed oligonucleotides may include oligonucleotides which hybridize to a specific region of BIN1 nucleic acid. In certain embodiments, multiple copies of a first oligonucleotide which specifically hybridizes to a first region of BIN1 nucleic acid are arrayed. In certain embodiments, multiple copies of first and a second oligonucleotide which specifically hybridize to a first and a second region of BIN1 nucleic acid, respectively, are arrayed, and so on. In certain embodiments, the BIN1 expression level is determined by mean values of the signal from each of these oligonucleotides. In certain embodiments, the array may also include oligonucleotides which specifically hybridize to nucleic acid of a normalizing gene, such as a housekeeping gene or other genes known not to be significantly differentially expressed in diseased versus normal tissue, for example, CaV 1.2.

Immunohistochemical methods may also be used for detecting the expression levels of BIN1. Thus, antibodies or antisera, such as, polyclonal antisera and monoclonal antibodies specific for BIN1 may be used to assess BIN1 expression. The antibodies can be detected by direct labeling of the antibodies themselves, for example, with radioactive labels, fluorescent labels, hapten labels such as biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Optionally, BIN1 expression in a tissue sample from a patient may be compared to BIN1 expression in a normal tissue sample or in a normal subject.

In certain cases, the amount of BIN1 protein present in a biological sample may be determined by a Western blot. For example, proteins present in the whole cell lysate from a biological sample may be separated by SDS-PAGE; the separated proteins transferred to a nitrocellulose membrane; BIN1 detected by using an antibody or antiserum specific for BIN1 or a specific isoform of BIN1. At least one normalizing protein, for example, Cav1.2 or a housekeeping protein such as GAPDH can also be detected simultaneously or in parallel and used to normalize the BIN protein expression levels. In alternative embodiments, BIN1 expression level may be determined by performing a BIN1 immunoprecipitation using an excess of anti-BIN1 antibody, followed by separation of the immunoprecipitate by SDS-PAGE; the separated proteins transferred to a nitrocellulose membrane; and detected by staining the gel, e.g., by Coomassie Blue or silver staining. Immunoprecipitation of a control protein such as GAPDH or ubiquitin may also be carried out either simultaneously or in parallel. Optionally, the same procedure may be carried out on corresponding normal tissue or from a sample from a normal subject.

Optionally, the BIN1 polypeptide, nucleic acid, or fragments of said polypeptides or nucleic acids detected is human. Optionally, BIN1 polypeptide, nucleic acid, or fragments of said polypeptides or nucleic acids detected is non-human (e.g., rodent, equine, canine, or feline).

There are a variety of BIN1 sequences that are disclosed on Genbank, and these sequences and others are herein incorporated by reference in their entireties as are individual subsequences or fragments contained therein. As used herein, BIN1 refers to the BIN1 and homologs, variants, and isoforms thereof. DNA and mRNA sequences for these polypeptides may also be determined to detect BIN1 expression levels in a biological sample.

The nucleotide and amino acid sequences of human skeletal muscle-specific BIN1 isoform 8 can be found at GenBank Accession Nos. NM_004305.3 and NP_04296.1 (SEQ ID NO:1), respectively. By way of another example, the nucleotide and amino acid sequences of BIN1 isoforms 1-7, 9, and 10 can be found at GenBank Accession Nos. NM_139343.2 and NP_647593.1 for isoform 1; NM_139344.2 and NP_647594.1 for isoform 2; NM_139345.2 and NP_647595.1 for isoform 3; NM_139346.2 and NP_647596.1 for isoform 4; NM_139347.2 and NP_647597.1 for isoform 5; NM_139348.2 and NP_647598.1 for isoform 6; NM_139349.2 and NP_647599.1 for isoform 7; NM_139350.2 and NP_647600.1 for isoform 9; and NM_139351.2 and NP_647601.1 for isoform 10.

Thus, provided are the nucleotide sequences of BIN1 comprising a nucleotide sequence at least about 70%, 75%, 80%, 85%, 90%, 95%, 98%, 99% or more identical to the nucleotide sequences of the aforementioned GenBank Accession Numbers. Also provided are amino acid sequences of BIN1 comprising an amino acid sequence at least about 70%, 75%, 80%, 85%, 90%, 95%, 98%, 99% or more identical to the sequences of the aforementioned GenBank Accession Numbers.

Antibodies that bind the polypeptides described above, including BIN1, or fragments thereof, can be used to detected BIN1 expression in a biological sample. For example, the polypeptides described above can be used to produce antibodies or fragments thereof to BIN1.

Provided are isolated antibodies or fragments thereof that specifically bind to BIN1 polypeptide that is expressed specifically in skeletal muscle. Optionally, the BIN1 polypeptide is a skeletal muscle specific BIN1 isoform. Optionally, the BIN1 isoform is BIN1 isoform 8. Optionally, the muscle specific BIN1 isoform comprises SEQ ID NO:1. Optionally, the muscle specific BIN1 isoform comprises SEQ ID NO:2. Optionally, the antibody specifically binds SEQ ID NO:2.

The isolated antibodies or fragments thereof that specifically bind to skeletal muscle BIN1 can, for example, have the same epitope specificity as an antibody or fragment with a light chain with polypeptide sequences (complementarity determining regions or CDRs) comprising SEQ ID NO:8, SEQ ID NO:9, and SEQ ID NO:10; SEQ ID NO:18, SEQ ID NO:19, and SEQ ID NO:20; or SEQ ID NO:28, SEQ ID NO:29, and SEQ ID NO:30, and a heavy chain with polypeptide sequences comprising SEQ ID NO:11, SEQ ID NO:12, and SEQ ID NO:13; SEQ ID NO:21, SEQ ID NO:22, and SEQ ID NO:23; or SEQ ID NO:31, SEQ ID NO:32, and SEQ ID NO:33. Optionally, the antibody or fragment comprises a light chain comprising SEQ ID NO:5, SEQ ID NO:15, or SEQ ID NO:25. Optionally, the antibody or fragment comprises a heavy chain comprising SEQ ID NO:7, SEQ ID NO:17, or SEQ ID NO:27. The light chain can, for example, comprise polypeptide sequences (CDRs) comprising SEQ ID NO:8, SEQ ID NO:9, and SEQ ID NO:10; SEQ ID NO:18, SEQ ID NO:19, and SEQ ID NO:20; or SEQ ID NO:28, SEQ ID NO:29, and SEQ ID NO:30. The heavy chain can, for example, comprise polypeptide sequences (CDRs) comprising SEQ ID NO:11, SEQ ID NO:12, and SEQ ID NO:13; SEQ ID NO:21, SEQ ID NO:22, and SEQ ID NO:23; or SEQ ID NO:31, SEQ ID NO:32, and SEQ ID NO:33.

As used herein, the term antibody encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term variable is used herein to describe certain portions of the antibody domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector functions, such as participation of the antibody in antibody-dependent cellular toxicity.

As used herein, the term epitope is meant to include any determinant capable of specific interaction with the provided antibodies. Epitopic determinants usually consist of chemically active surface groupings of molecules such as amino acids or sugar side chains and usually have specific three dimensional structural characteristics, as well as specific charge characteristics. Identification of the epitope that the antibody recognizes is performed as follows. First, various partial structures of the target molecule that the monoclonal antibody recognizes are prepared. The partial structures are prepared by preparing partial peptides of the molecule. Such peptides are prepared by, for example, known oligopeptide synthesis technique or by incorporating DNA encoding the desired partial polypeptide in a suitable expression plasmid. The expression plasmid is delivered to a suitable host, such as E. coli, to produce the peptides. For example, a series of polypeptides having appropriately reduced lengths, working from the C- or N-terminus of the target molecule, can be prepared by established genetic engineering techniques. By establishing which fragments react with the antibody, the epitope region is identified. The epitope is more closely identified by synthesizing a variety of smaller peptides or mutants of the peptides using established oligopeptide synthesis techniques. The smaller peptides are used, for example, in a competitive inhibition assay to determine whether a specific peptide interferes with binding of the antibody to the target molecule. If so, the peptide is the epitope to which the antibody binds. Commercially available kits, such as the SPOTs Kit (Genosys Biotechnologies, Inc., The Woodlands, Tex.) and a series of multipin peptide synthesis kits based on the multipin synthesis method (Chiron Corporation, Emeryvile, Calif.) may be used to obtain a large variety of oligopeptides.

The term antibody or fragments thereof can also encompass chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain binding activity to BIN1 expressed specifically in skeletal muscle are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York (1988)).

Also included within the meaning of antibody or fragments thereof are conjugates of antibody fragments and antigen binding proteins (single chain antibodies) as described, for example, in U.S. Pat. No. 4,704,692, the contents of which are hereby incorporated by reference in their entirety.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies, A Laboratory Manual. Cold Spring Harbor Publications, New York (1988). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. The immunizing agent can be BIN1 specifically expressed in skeletal muscle or an immunogenic fragment thereof.

Generally, either peripheral blood lymphocytes (PBLs) are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium") substances that prevent the growth of HGPRT-deficient cells.

Immortalized cell lines useful here are those that fuse efficiently, support stable high level expression of antibody by the selected antibody-producing cells, and are sensitive to a medium such as HAT medium. Immortalized cell lines include murine myeloma lines, which can be obtained, for instance, from the Salk Institute Cell Distribution Center; San Diego, Calif. and the American Type Culture Collection; Rockville, Md. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York (1987) pp. 51-63).

The culture medium in which the hybridoma cells are cultured can then be assayed for the presence of monoclonal antibodies directed against BIN1 specifically expressed in skeletal muscle or selected epitopes thereof. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art, and are described further in Harlow and Lane Antibodies, A Laboratory Manual, Cold Spring Harbor Publications, New York (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for BIN1 specifically expressed in skeletal muscle and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

One method of producing proteins comprising the provided antibodies or polypeptides is to link two or more peptides or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry (Applied Biosystems, Inc.; Foster City, Calif.). Those of skill in the art readily appreciate that a peptide or polypeptide corresponding to the antibody provided herein, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer Verlag Inc., NY). Alternatively, the peptide or polypeptide can by independently synthesized in vivo. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776 779 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al., FEBS Lett. 307:97-101 (1992); Clark et al., J. Biol. Chem. 269:16075 (1994); Clark et al., Biochemistry 30:3128 (1991); Rajarathnam et al., Biochemistry 33:6623-30 (1994)).

Alternatively, unprotected peptide segments can be chemically linked where the bond formed between the peptide segments as a result of the chemical ligation is an unnatural (non peptide) bond (Schnolzer et al., Science 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-267 (1992)).

The provided polypeptide fragments can be recombinant proteins obtained by cloning nucleic acids encoding the polypeptide in an expression system capable of producing the polypeptide fragments thereof, such as a bacterial, adenovirus or baculovirus expression system. For example, one can determine the active domain of an antibody from a specific hybridoma that can cause a biological effect associated with the interaction of the antibody with BIN1 specifically expressed in skeletal muscle. For example, amino acids found to not contribute to either the activity or the binding specificity or affinity of the antibody can be deleted without a loss in the respective activity.

The provided fragments, whether attached to other sequences, can also include insertions, deletions, substitutions, or other selected modifications of particular regions or specific amino acids residues, provided the activity of the fragment is not significantly altered or impaired compared to the nonmodified antibody or epitope. These modifications can provide for some additional property, such as to remove or add amino acids capable of disulfide bonding, to increase its bio longevity, to alter its secretory characteristics, and the like. In any case, the fragment can possess a bioactive property, such as binding activity, regulation of binding at the binding domain, and the like. Functional or active regions may be identified by mutagenesis of a specific region of the protein, followed by expression and testing of the expressed polypeptide. Such methods are readily apparent to a skilled practitioner in the art and can include site specific mutagenesis of the nucleic acid encoding the antigen. (Zoller et al., Nucl. Acids Res. 10:6487-500 (1982)).

Further provided herein is a humanized or human version of the antibody. Optionally, the humanized or human antibody comprises at least one complementarity determining region (CDR) of an antibody having the same epitope specificity as an antibody produced by the hybridoma cell line disclosed herein. For example, the antibody can comprise all CDRs of an antibody having the same epitope specificity as an antibody produced by the hybridoma cell line.

Optionally, the humanized or human antibody can comprise at least one residue of the framework region of the monoclonal antibody produced by a disclosed hybridoma cell line. Humanized and human antibodies can be made using methods known to a skilled artesian; for example, the human antibody can be produced using a germ-line mutant animal or by a phage display library.

Antibodies can also be generated in other species and humanized for administration to humans. Alternatively, fully human antibodies can also be made by immunizing a mouse or other species capable of making a fully human antibody (e.g., mice genetically modified to produce human antibodies) and screening clones that bind BIN1 specifically expressed in skeletal muscle. See, e.g., Lonberg and Huszar, Int. Rev. Immunol. 13:65-93, (1995), which is incorporated herein by reference in its entirety for methods of producing fully human antibodies. As used herein, the term humanized and human in relation to antibodies, relate to any antibody which is expected to elicit a therapeutically tolerable weak immunogenic response in a human subject. Thus, the terms include fully humanized or fully human as well as partially humanized or partially human.

Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-525 (1986); Riechmann et al., Nature, 332:323-327 (1988); and Presta, Curr. Op. Struct. Biol., 2:593-596 (1992)).

Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321:522-525 (1986); Riechmann et al., Nature 332:323-327 (1988); or Verhoeyen et al., Science 239:1534-1536 (1988), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The nucleotide sequences encoding the provided antibodies can be readily isolated and sequenced using conventional procedures (e.g., by using oligonucleotide probes that are capable of binding specifically to genes encoding the heavy and light chains of murine antibodies). These nucleotide sequences can also be modified, or humanized, for example, by substituting the coding sequence for human heavy and light chain constant domains in place of the homologous murine sequences (see, e.g., U.S. Pat. No. 4,816,567). The nucleotide sequences encoding any of the provided antibodies can be expressed in appropriate host cells. These include prokaryotic host cells including, but not limited to, *E. coli*, *Bacillus subtilus*, other enterobacteriaceae such as *Salmonella typhimurium* or *Serratia marcesans*, and various *Pseudomonas* species. Eukaryotic host cells can also be utilized. These include, but are not limited to, yeast cells (for example, *Saccharomyces cerevisiae* and *Pichia pastoris*), and mammalian cells such as VERO cells, HeLa cells, Chinese hamster ovary (CHO) cells, W138 cells, BHK cells, COS-7 cells, 293T cells and MDCK cells. The antibodies produced by these cells can be purified from the culture medium and assayed for binding, activity, specificity or any other property of the monoclonal antibodies by utilizing the methods set forth herein and standard in the art.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA 90:2551-255 (1993); Jakobovits et al., Nature 362:255-258 (1993); Bruggemann et al., Year in Immuno. 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, ed., p. 77 (1985); Boerner et al., J. Immunol., 147(1):86-95 (1991)).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Materials and Methods
Subject Characteristics.

Dogs were selected for determination of BIN1 levels. The dogs used were at minimum age of six months and a minimum body weight of 2.3 kilograms (kg). The dogs were outwardly healthy with no indication of active diseases presently or in their past medical history. The dogs were excluded for the following reasons: a) had exercised or had an elevated temperature within the previous 96 hours; b) had an intractable disposition precluding safe restraint without risk to dog or personnel; c) had a disease or condition such as a significant skin disease (e.g., dermatitis, otitis), a musculoskeletal disorder (e.g., lameness, neurologic disorders, muscle atrophy), an abdominal disorder (e.g., palpable masses, abnormalities with organ shape), a cardiac disease (e.g., tachycardia, weak/abnormal peripheral pulse, significant heart murmurs), and a respiratory disease (e.g., increased lung sounds); d) had an inability to obtain sufficient blood for both plasma BIN1 testing (0.5 ml minimum) and plasma chemistry panel submission (0.5 ml minimum); and e) had plasma chemistry findings of significant organ dysfunction (e.g., elevated creatine, increased liver enzymes, etc.).

Clinical Evaluation of Muscle Mass (MM).

A mechanism to provide a subjective assessment of a dog's muscle mass and condition was developed. The caudal aspects of hindlimb musculature (e.g., semitendinosus, semimembrinosis, gracilis, adductor cruris caudalis, and biceps femoris muscles) were palpated from caudal approach, at the level of the mid-femur, to estimate the muscle mass of a particular dog. This site was chosen as the hindlimb provided the primary force for locomotion in canines, and the condition of this muscle group is indicative of the overall muscular conditioning. This muscle group is responsible for extension of the hip joint as well as both extension and flexion of the stifle joint, and extension of the tarsal joint (Evans and Christensen, Miller's Anatomy of the Dog, $2^{nd}$ Ed., W B Saudners, pp 383-400 (1979)). Palpation of this area is readily performed with the dog in standing position, requiring minimal restraint. With the leg in the relaxed position and the stifle in extension, accurate, relaxed muscle tone can be assessed (as opposed to a state of muscle tension due to heavy restraint or other physiologic stressors). There is additionally an absence of significant fat deposits, such as truncal fat in an obese dog, facilitating palpation of isolated muscle bellies.

A scale of 1-4 was used to assess muscle mass. Level 1 is characterized by very poor muscle mass and tone such that the caudal aspect of the mid-femur may be readily palpated from a caudal approach, with little obstruction from muscle bellies. The muscles themselves are soft/flaccid. This condition can be found in a dog that spends close to its entire life in a cage with little to no opportunity for exercise. Level 2 is characterized by a subnormal muscle mass and tone such that from a caudal approach the caudal aspect of the mid-femur may not be palpated due to obstruction from the muscle bellies, however, the lateral and medial aspects of the femur may be just palpated. The muscles have some tone, and reasonable mass. This condition can be found in a dog that occasionally exercises such as a sedentary housepet that walks outside to urinate or defecate and returns to lie down. Level 3 is characterized by average muscle mass and tone such that from a caudal approach the mid-femur cannot be palpated at all due to obstruction by the muscle bellies. There is a good tone felt when the muscles are relaxed. This condition can be found in a dog that is an active housepet, with frequent leash-walks. Level 4 is characterized by above-average muscle mass and tone such that the muscles feel hard in a relaxed state and bulge significantly in comparison to the area of the mid-femur, when palpated from a caudal approach at the level of the mid-femur. This condition can be found in a dog that spends a significant amount of time outside running in a large yard.

Venipuncture Procedure in Canine Population.

Each dog was restrained in sternal recumbancy. The hair of the dog was clipped for a 1 inch window over the jugular vein and the skin was prepped with alcohol. A finger was placed in the jugular groove to act as a tourniquet, and a 12.0 ml syringe with a 21 gauge-1 inch needle was used for venipuncture. Between 3.0 to 7.0 mls of blood was collected. A finger was placed over the puncture site, and the needle and syringe were removed from the dog and pressure was applied to the puncture site to prevent a hematoma. The blood was placed in a 7.0 ml glass EDTA tube by removing both the needle and tube stopper gently and injecting the blood into the side of the tube. The stopper was replaced and the anticoagulant was mixed with the blood by gently inverting the tube 20 times.

Plasma Acquisition in Bovine Population.

Samples were collected at a commercial cattle slaughterhouse. Cattle were slaughtered according to conventional procedures including severing of the jugular vein for exsanguinations. During the process of exsanguinations and after a steady flow of blood developed, 7.0 ml of whole blood was collected into a glass EDTA tube by removing the tube stopper. The stopper was replaced and the anticoagulant was mixed with the blood by gently inverting the tube 20 times. Collection of the blood samples did not affect the pace of handling the animal prior to slaughter, or handling the carcass post slaughter.

Plasma Collection and Storage.

Within 3 hours of collection of the blood, the EDTA tube was centrifuged for 15 minutes at a speed of 3000 rotations per minute (RPM). The supernatant (plasma) was removed, carefully avoiding collection of red blood cells. The plasma was separated into two equal aliquots, placed into 2 ml cryovials, and frozen at $-20°$ C.

Plasma Chemistry Analysis.

Within three days of freezing, the plasma samples were thawed and analyzed with an Olympus AU2700 blood chemistry analyzer at a commercial reference laboratory (Antech Diagnostics; Tampa, Fla.). The tests performed included: total protein; albumin; globulin; serum glutamic oxaloacetic transaminase (SGOT); serum glutamic pyruvic transaminase (SGPT); alkaline phosphatase; gamma-glutamyl transpeptidase (GGTP); total bilirubin; urea nitrogen; creatine; phosphorous; glucose; calcium; magnesium; sodium; potassium; chloride; cholesterol; triglycerides; amylase; lipase; and creatine phosphokinase levels. Samples with high muscle contaminant (creatine kinase>500 IU/L) were not used in the analysis.

Detection of Serum BIN1 Protein by Capture ELISA.

Novel customized rabbit polyclonal anti-skeletal BIN1 (anti-skBIN1) antibodies were raised against antigen of the skeletal specific phosphoinositol binding domain of BIN1 (transcript variant 8) (Anaspec; San Jose, Calif.). Round bottomed 96-well plates were coated at 4° C. for 16 hours with mouse anti-BIN1 (1/1000) or anti-skBIN1 (1/1000) diluted in 0.1 M sodium carbonate buffer, pH 9.0. The plates were washed three times with tris-buffered saline tween-20™ (TBST) to remove unbound antibody and blocked for 1 hour at room temperature with 5% bovine serum albumin (BSA) in TBST (blocking buffer). 100 ml of each serum sample was added, in triplicate, and plates were incubated for 1 hour at room temperature with rotation. The samples were then aspirated and plates were washed twice quickly and three times for 5 minutes with TBST. Goat anti-BIN1 (1/1000 in blocking buffer) was then applied as a detection antibody, and the plates were incubated for 1 hour at room temperature with rotation. The detection antibody was then aspirated and the plates were washed twice quickly, followed by three times for 5 minutes with TBST. The plates were subsequently incubated for 1 hour at room temperature with HRP-conjugated donkey anti-goat IgG (1/4000 in blocking buffer) before two quick washes and three 5 minute washes with TBST. TMB substrate was added and plates were incubated in the dark for 1 hour before reaction termination with 1 N hydrocholic acid (HCL). Following the reaction termination, the plates were read using the ELx800 BioTek microplate spectrophotometer (BioTek; Winooski, Vt.) and OD values were determined at 405 nm. Values were normalized to one tenth the OD of a standard canine serum sample, which was included on all plates. The one-way ANOVA with Bonferroni post-test was used for statistical analysis of BIN1 or skBIN1 levels grouped by MM score. For correlation of scatter plots, a linear regression was applied and slopes of 95% confidence intervals were presented in graphs.

Sequencing of Monoclonal skBIN1 Antibodies.

Total RNA was extracted from the hybridoma using a Qiagen RNA extraction kit (Qiagen; Valencia, Calif.). Using a QIAGEN® OneStep RT-pCR kit, RT-PCR was performed with primer sets specific for the heavy and light chains. For each RNA sample, 12 individual heavy chain and 11 light chain RT-PCR reactions were set up using degenerate forward primer mixtures covering the leader sequences of variable regions. Reverse primers are located in the constant regions of heavy and light chains. No restriction sites were engineered into the primers.

The RT-PCR products from the first-round reactions were further amplified in the second-round PCR. 12 individual heavy chain and 11 light chain RT-PCR reactions were set up using semi-nested primer sets specific for antibody variable regions. After the PCR reactions were finished, the PCR reaction was run on an agarose gel to visualize the amplified DNA fragments. The correct antibody variable region DNA fragments should have a size between 400-500 base pairs. The positive PCR bands were cloned and 10-20 clones per sample were sequenced.

Results

A large canine study was undertaken to determine the correlation between serum BIN1 and skeletal specific BIN1 levels and clinically obtained parameters (e.g., age, weight, and muscle mass). 34 healthy purebred Havanese and Sheltie canines ranging from 0.5 to 10 years were studied. The canines were selected for the study using the criteria provided above, and Tables 1 and 2 show a breakdown of the canines used in the study. Serum was obtained from the canines, and the serum was used to measure levels of BIN1 protein by a capture enzyme-linked immunosorbent assay (ELISA).

Figure 2:
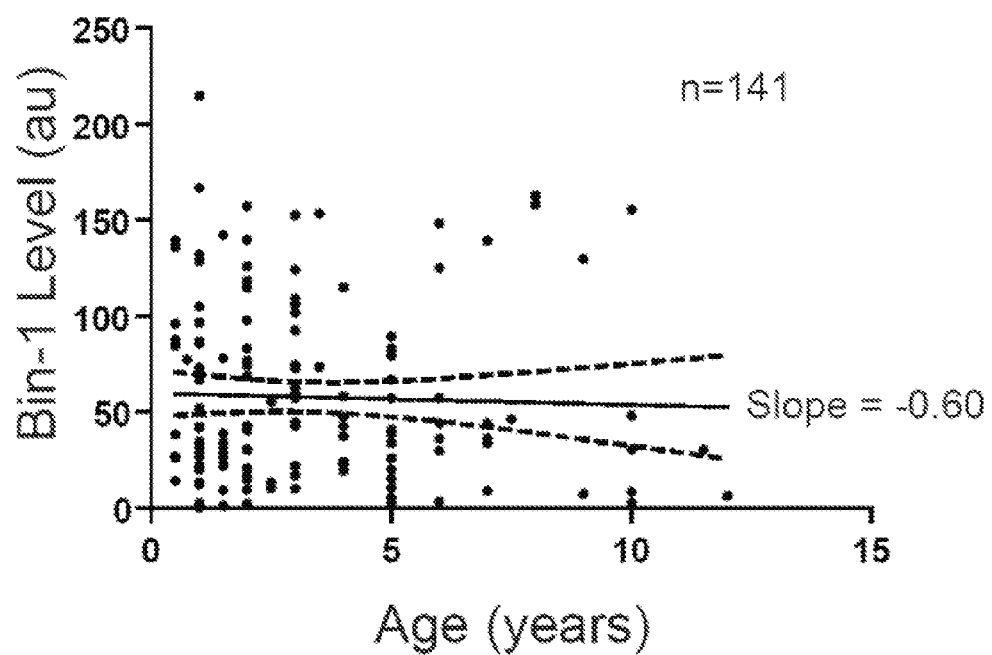
FIG. 2 is a scatter plot of measured BIN1 levels (A.U.) versus age (years) in canine subjects. A line fit by linear regression has a slope of −0.6 indicating a potential dependency of BIN1 on age.
Figure 3:
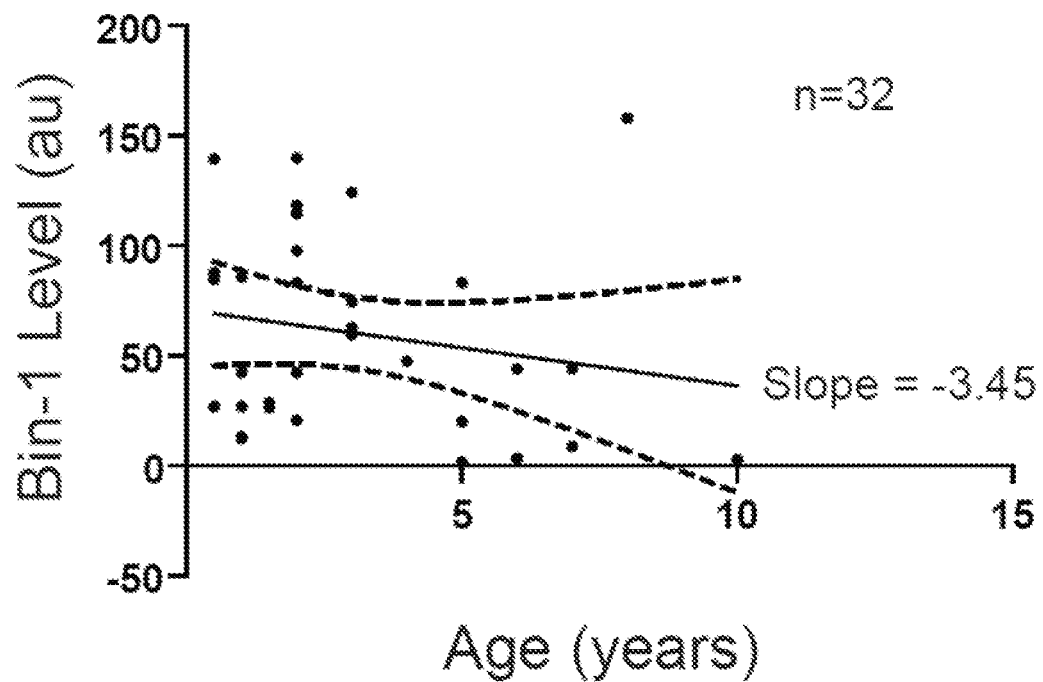
FIG. 3 is a scatter plot of measured BIN1 levels (A.U.) versus age (years) in two small breeds of canines. To assess for breed dependence of BIN1, a scatter plot was obtained between BIN1 and age (years) in two breeds which were both of similar size and also had the two largest numbers of dogs in a canine study (Sheltie, n=20, average weight=9.5 kg and Havanese, n=12, average weight=4.6 kg). A line fit by linear regression has a slope of −3.5 indicating, in these isolated breeds, a strong inverse correlation between BIN1 and age. These data indicate BIN1 decreases with age, within a particular breed of canine.
Figure 4:
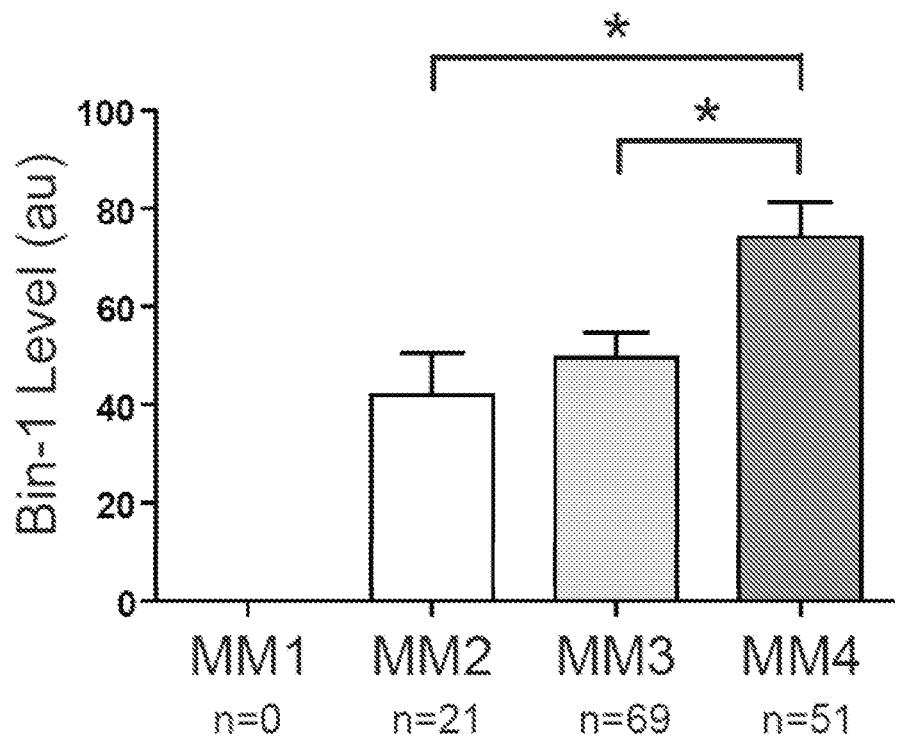
FIG. 4 is a bar graph of measured BIN1 levels (A.U.) against muscle mass (MM) in canine subjects. The canines with the largest MM (4) have significantly greater levels of BIN1 than canines with less muscle mass (scored either as 3 or 2). No canines were scored with a muscle mass of 1. *p<0.05. These data indicate that BIN1 correlates directly with clinically assessed muscle mass, confirming the inverse correlation between BIN1 and age in FIG. 3 is secondary to muscle atrophy with age.

The levels of BIN1 were compared to the weight of the canines across all species examined (FIG. 1), to the age of the canines across all species examined (FIG. 2), to the age of the canines in two specific species examined (FIG. 3), and to the muscle mass of the canines (FIG. 4). It was found that there is little dependency of BIN1 on weight (FIG. 1) and that there is a potential dependency of BIN1 on the age (FIG. 2) when the data were plotted for all species of dogs examined. When the data were limited to two particular species (Sheltie and Havanese), for which the most data were present, it was found that there was an inverse correlation between BIN1 levels and the age of the dog (FIG. 3). When the levels of BIN1 were measured against a clinical score for muscle mass, it was found that high BIN1 levels correlate strongly with high levels of muscle mass (FIG. 4).

TABLE 1

Canines used to measure BIN1 levels

| Breed | Count | Avg Age (yrs) | Avg Weight (kg) | Avg MM |
|---|---|---|---|---|
| Australian Cattle Dog | 1 | 7.5 | 15.0 | 4.0 |
| Australian Shepherd | 2 | 4.0 | 20.0 | 3.5 |
| Basenji | 2 | 1.8 | 5.5 | 3.0 |
| Beagle | 2 | 3.5 | 11.5 | 3.5 |

TABLE 1-continued

Canines used to measure BIN1 levels

| Breed | Count | Avg Age (yrs) | Avg Weight (kg) | Avg MM |
|---|---|---|---|---|
| Beauceron | 1 | 1.0 | 35.0 | 4.0 |
| Belgian Tervleren | 4 | 6.0 | 23.5 | 3.8 |
| Berger Piccard | 4 | 3.1 | 24.5 | 4.5 |
| Bichon | 1 | 10.0 | 9.0 | 2.0 |
| Bichon Frise | 1 | 1.0 | 6.0 | 2.0 |
| Border Collie | 7 | 2.7 | 16.1 | 3.9 |
| Boxer | 2 | 1.5 | 27.0 | 3.0 |
| Chinese Crested | 1 | 5.0 | 3.0 | 2.0 |
| Corgi | 1 | 3.0 | 14.0 | 4.0 |
| Dalmation | 3 | 2.5 | 25.3 | 3.0 |
| French Bulldog | 3 | 2.2 | 12.0 | 2.7 |
| German Wire Haired Pointer | 1 | 1.5 | 20.0 | 4.0 |
| Golden Retriever | 8 | 3.4 | 30.3 | 3.1 |
| Great Dane | 2 | 1.3 | 54.0 | 4.0 |
| Great Pyranees Mix | 1 | 4.0 | 39.0 | 3.0 |
| Havanese | 12 | 3.4 | 4.6 | 2.6 |
| King Charles Cavalier Spaniel | 7 | 2.1 | 4.0 | 2.4 |
| Labrador Retreiver | 9 | 5.6 | 38.0 | 3.6 |
| Mastiff | 1 | 1.0 | 62.0 | 4.0 |
| Min Pin | 3 | 1.8 | 5.3 | 2.7 |
| Mix | 3 | 4.3 | 23.8 | 3.7 |
| Nova Scotia Duck Tolling Retriever | 2 | 6.0 | 17.0 | 3.5 |
| Papillon | 2 | 1.8 | 2.0 | 3.5 |
| Pit Bull | 3 | 1.2 | 20.7 | 4.0 |
| Poodle | 4 | 2.0 | 5.5 | 3.0 |
| Portugese Water Dog | 2 | 6.5 | 19.0 | 3.0 |
| Pug | 2 | 8.0 | 6.6 | 2.5 |
| Rat Terrier | 1 | 4.0 | 9.0 | 3.0 |
| Rhodesian Ridgeback | 7 | 2.4 | 38.3 | 3.4 |
| Rottweiler | 1 | 2.0 | 40.0 | 4.0 |
| Samoyed | 1 | 4.0 | 20.0 | 3.0 |
| Sheltie | 20 | 2.9 | 9.5 | 3.4 |
| Shih Tzu | 1 | 10.0 | 3.5 | 2.0 |
| Silky Terier | 5 | 1.4 | 4.0 | 3.6 |
| Standard Poodle | 3 | 3.0 | 19.7 | 3.0 |
| Tibetan Mastiff | 3 | 1.9 | 46.7 | 3.0 |
| Vizsla | 1 | 3.0 | 24.0 | 4.0 |
| Whippet | 1 | 7.0 | 13.0 | 3.0 |
| ALL BREEDS | 141 | 3.6 | 19.7 | 3.3 |

TABLE 2

Canine characteristics. Live canines used for clinical examination of MM and for venous skBIN1 levels (MM is clinically assessed muscle mass).

| Breed | Count | Age (yrs) | Weight (kg) | MM |
|---|---|---|---|---|
| Havanese | 15 | 4.1 | 4.6 | 2.6 |
| Sheltie | 19 | 3.3 | 9.5 | 3.5 |
| Both Breeds | 34 | 3.6 | 7.4 | 3.1 |

Figure 5:
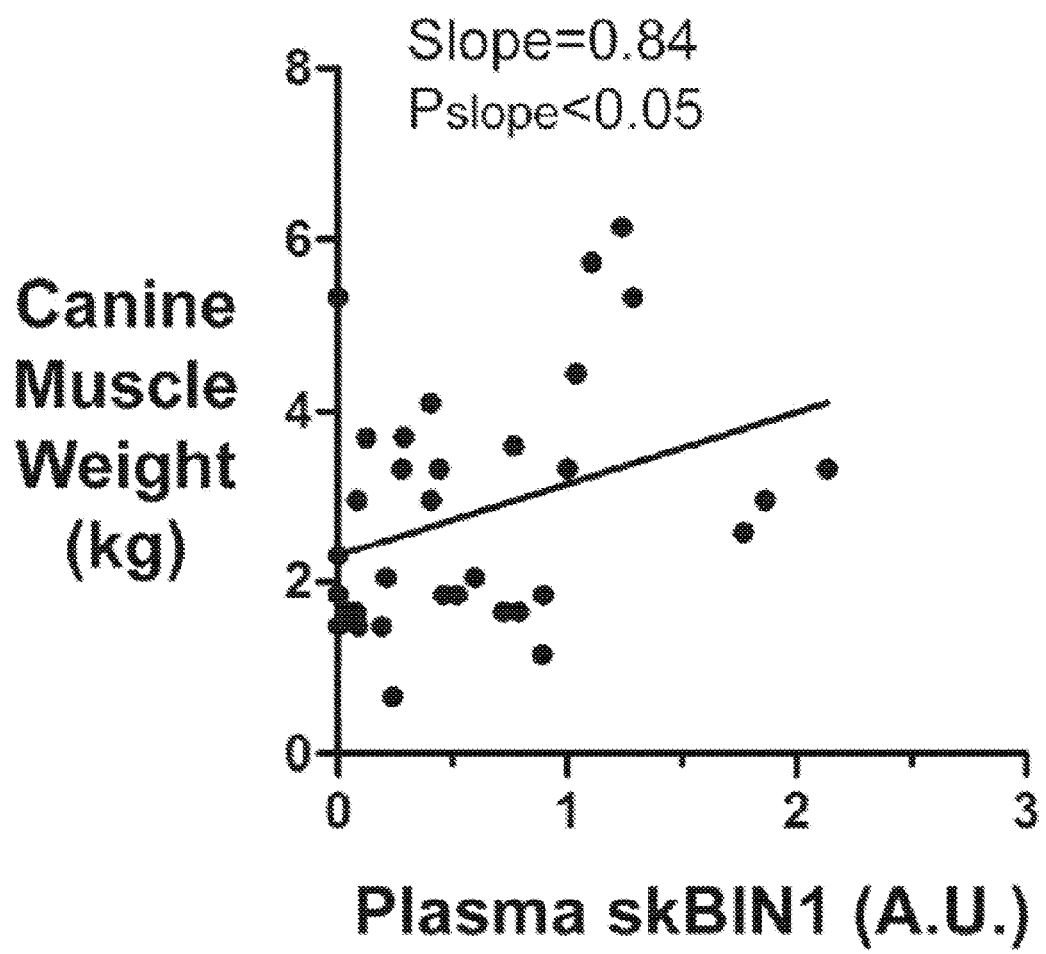
FIG. 5 shows that plasma skBIN1 predicts clinically assessed canine muscle weight.

The levels of skBIN1 were also compared to the muscle weight across all canines examined. Muscle weight was determined as 25% of measured live body weight plus an additional 4% of body weight for every point of physically palpated muscle mass (MM, scored 1 to 4). Results are shown in FIG. 5. Canine muscle weight increases in direct proportion to measured skBIN1. The resulting slope is 08 kg/A.U. (P<0.05). This statistically significant correlation suggests that canine muscle weight can be predicted by venous blood samples skBIN1. Therefore, skBIN1 prediction of canine muscle weight is not dependent on a particular physical examination.

Figure 6:
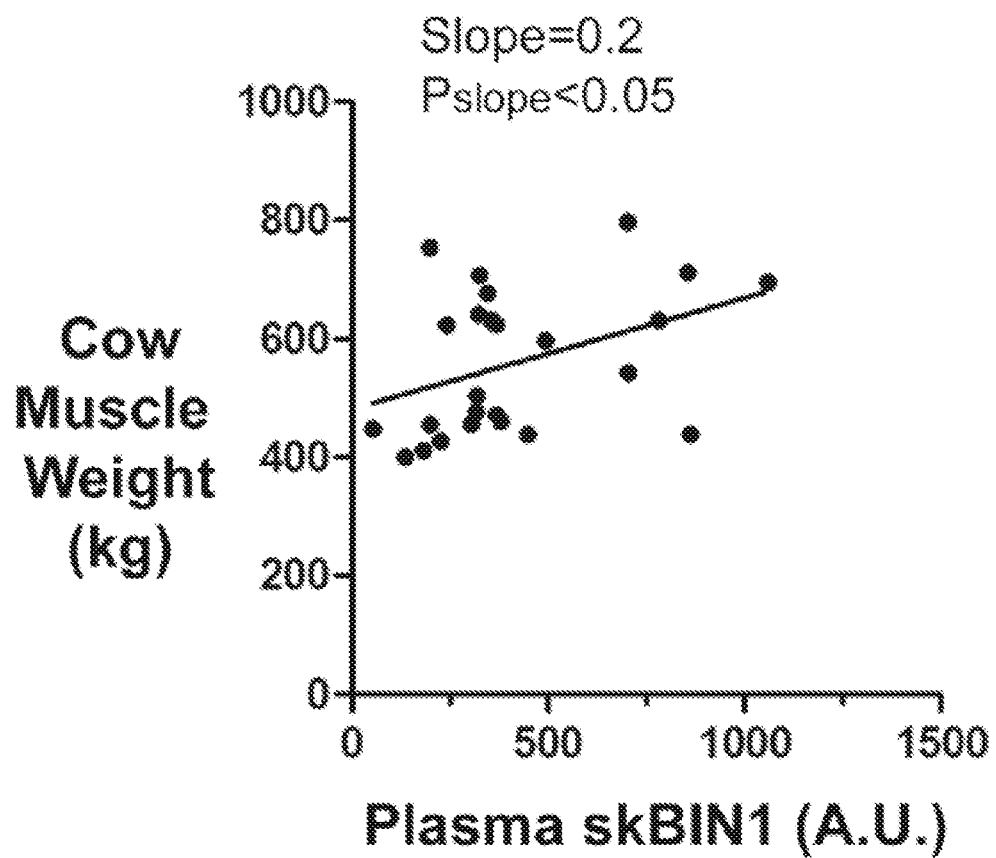
FIG. 6 shows plasma skBIN1 predicts post-slaughter dressed bovine muscle weight.

The standard of muscle mass measurement is direct weight obtained from an animal carcass in which non-muscle structures are eliminated. At a commercial bovine slaughterhouse, blood was obtained from adult Holstein cows. Then, the hanging or dressed weigh was obtained. The dressed weight is a combination of skeletal muscle, intramuscular fat, and bone that is left behind following removal of the head, hide, hooves, viscera, and intracavitary fat. Typically, bone is 20% of this weight. Subtracting the estimated bone fraction from this otherwise directly measured muscle weight, the cows had an average muscle weight of 448.6 kg. FIG. 6 demonstrates measured cow muscle weight as a function of venous skBIN1 obtained at the time of slaughter. As with the canines, the cow data has a strong linear correlation between measured muscle weight and plasma based skBIN1 (slope is 0.2 kg/A.U., P<0.05). Of note, there is no significant correlation between skBIN1 and measured live weight of the cows (P=0.23), which is in agreement with the known difficulty of estimating beef yield from live animals.

Figure 7:
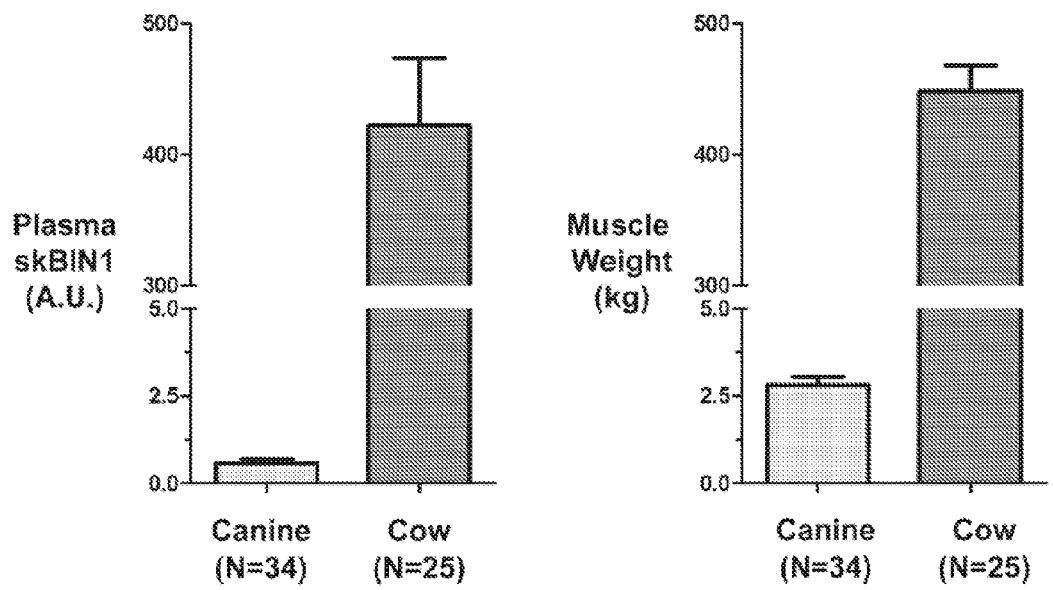
FIG. 7 shows plasma skBIN1 levels are proportionally higher in bovine relative to canine samples.

The slope of the cow muscle weight to skBIN1 (0.2 kg/A.U.) was similar to and actually lower than the slope of the canine muscle weight to skBIN1 (0.8 kg/A.U.). These slopes suggested that, despite the enormous difference in size of the cow to the dog, a unit increase in cow skBIN1 does not correspond to more total muscle compared to the dog. This observation was borne out by visualizing the ratios of mean skBIN1 versus the mean skeletal muscle for the two types of animals (FIG. 7). Mean skBIN1 of cow to canine is 422.0 to 0.6, whereas mean muscle weight of cow to canine is 448.6 to 2.8. Thus, skBIN1 is independent of mammalian size but rather corresponds to net animal muscle weight instead.

Human skBIN1 Levels.

Using the skeletal specific BIN1 antibody, human skBIN1 levels were assessed by ELISA. The fat percentage of the humans were also assessed by the 9-point caliper method, and measured regions included the chest, abdomen, thigh, bicep, tricep, subscapular, superiliac, lower back, and calf. The generic BIN1 antibody was also used to determine total BIN1 content in the plasma of the same patients. Non-fat percentage was the difference between fat percentage from the 9-point caliper measurements and 100%.

Figure 8:
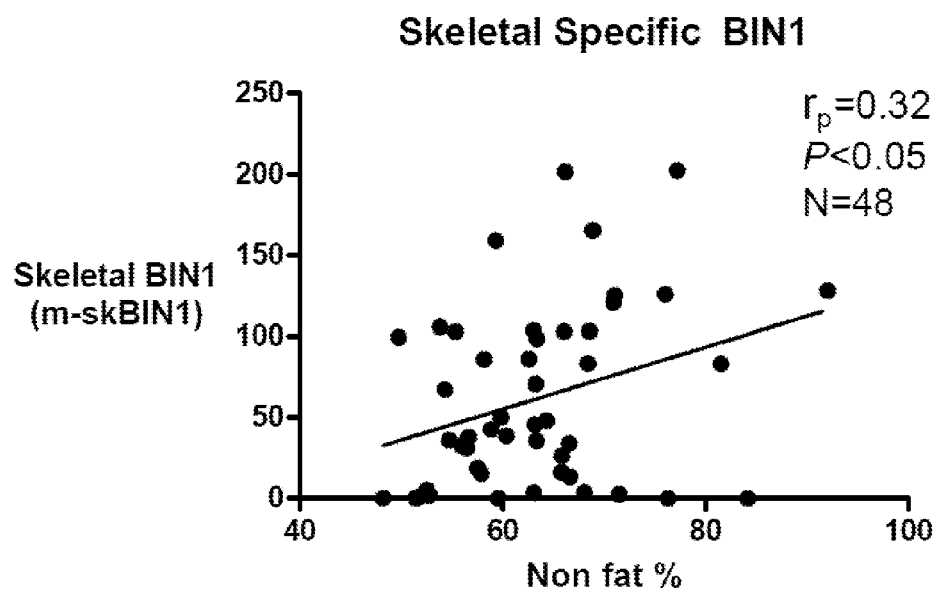
FIG. 8 shows a graph of the levels of plasma skBIN1 versus the non-fat percentage of healthy human subjects.
Figure 9:
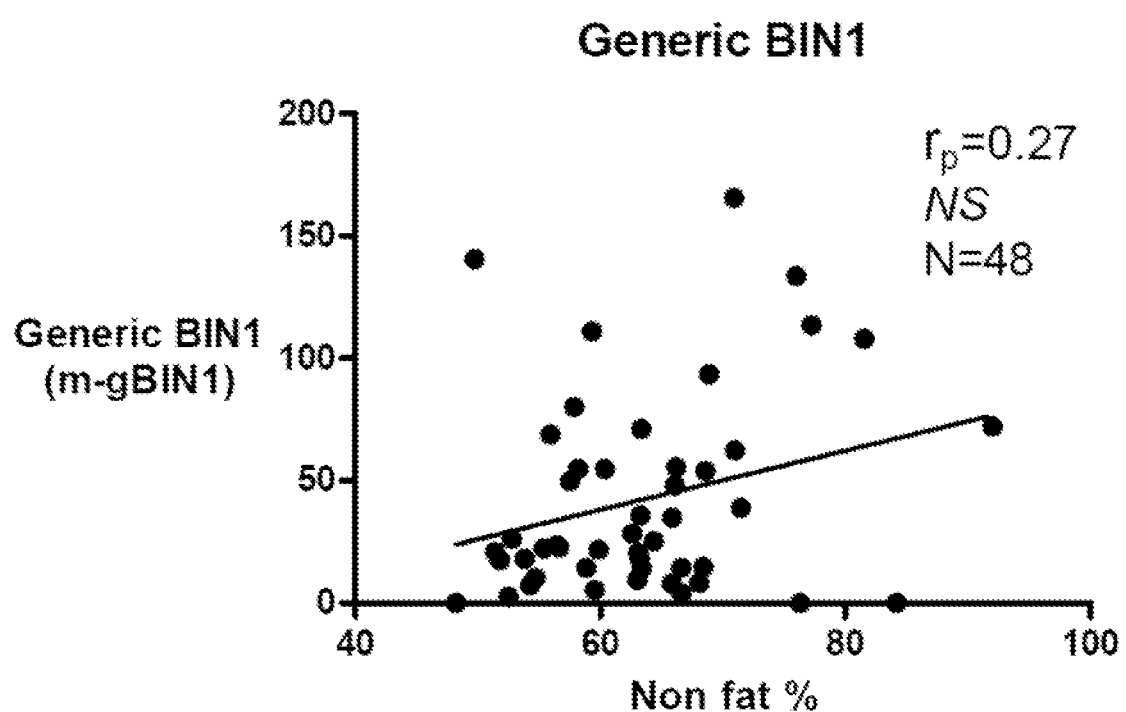
FIG. 9 shows a graph of the levels of plasma generic BIN1 versus the non-fat percentage of healthy human subjects.

A total of sixty subjects were studied. Eight patients were not included because of high plasma CPK (>250) indicating contaminating muscle damage during blood draw. Plasma BIN1 was determined in the other fifty-two subjects. Of these, four subjects had values that were inconsistent on serial assay. The remaining 48 subjects were used for the study (Table 3). FIG. 8 shows the results of ELISA determined skBIN1 levels versus non-fat percentage. FIG. 9 shows the results of ELISA determined generic BIN1 versus non-fat percentage. Note that there is a direct relationship between plasma BIN1 values and non-fat (lean) percentage. A linear fit to the data is statistically significant in the population detected with skBIN1 but not in the population detected with generic BIN1.

TABLE 3

Human patient characteristics.

| Total | Male | Female | Age (yr) | BMI | % Non-Fat |
|---|---|---|---|---|---|
| 48 | 10 | 38 | 38.3 ± 2.1 | 26.8 ± 0.9 | 63.4 ± 1.3% |

Sequencing of Monoclonal skBIN1 Antibodies.

Three hybridomas (MHC156, MHC157, and MHC158) that produce monoclonal skBIN1 antibodies were sent for sequencing to LakePharma (LakePharma; Belmont, Calif.). Briefly, total RNA was extracted from the hybridoma cells, reverse-transcription followed by polymerase chain reaction (RT-PCR) was performed and DNA for the variable heavy and variable light chains was amplified. Positive clones were identified by electrophoresis, and the positive DNA was cloned and sequenced.

Sequencing of the monoclonal antibody produced from hybridoma MHC 156 produced the following sequences: the nucleic acid and amino acid sequences of the variable region of the light chain (SEQ ID NOs:4 and 5) and the variable region of the heavy chain (SEQ ID NOs:6 and 7). Further analysis of the variable region of the light chain indicated a complementarity determining region 1 (CDR1) sequence of QDVSTA (SEQ ID NO:8), a CDR2 sequence of SASY (SEQ ID NO:9), and a CDR3 sequence of QQHYSTPLT (SEQ ID NO:10). Further analysis of the heavy chain indicated a CDR1 sequence of GYTFTRYY (SEQ ID NO:11), a CDR2 sequence of IYPGNVNT (SEQ ID NO:12), and a CDR3 sequence of AREGSYEYDEADY (SEQ ID NO:13).

Sequencing of the monoclonal antibody produced from hybridoma MHC 157 produced the following sequences: the nucleic acid and amino acid sequences of the variable region of the light chain (SEQ ID NOs:14 and 15) and the variable region of the heavy chain (SEQ ID NOs:16 and 17). Further analysis of the variable region of the light chain indicated a CDR1 sequence of QDVSTA (SEQ ID NO:18), a CDR2 sequence of SASY (SEQ ID NO:19), and a CDR3 sequence of QQHYSTPLT (SEQ ID NO:20). Further analysis of the heavy chain indicated a CDR1 sequence of GYTFTRYY (SEQ ID NO:21), a CDR2 sequence of IYPGNVNT (SEQ ID NO:22), and a CDR3 sequence of AREGSYEYDEADY (SEQ ID NO:23).

Sequencing of the monoclonal antibody produced from hybridoma MHC 158 produced the following sequences: the nucleic acid and amino acid sequences of the variable region of the light chain (SEQ ID NOs:24 and 25) and the variable region of the heavy chain (SEQ ID NOs:26 and 27). Further analysis of the variable region of the light chain indicated a CDR1 sequence of QSLLDSDGKTY (SEQ ID NO:28), a CDR2 sequence of LVSK (SEQ ID NO:29), and a CDR3 sequence of WQGTHFPYT (SEQ ID NO:30). Further analysis of the variable region of the heavy chain indicated a CDR1 sequence of GFNIKDYY (SEQ ID NO:31), a CDR2 sequence of IDPENGDT (SEQ ID NO:32), and a CDR3 sequence of NSDY (SEQ ID NO:33).

What is claimed is:

1. A method for determining relative total skeletal muscle weight in a human or veterinary subject, comprising:
   (a) detecting a level of skeletal muscle specific bridging integrator 1 (BIN1) isoform 8 expression in a biological sample from a human or veterinary subject by contacting the biological sample with an antibody that specifically binds to BIN1 isoform 8 and detecting the binding between BIN1 isoform 8 and the antibody that specifically binds to BIN1 isoform 8, wherein the biological sample is selected from the group consisting of blood, serum and plasma, and wherein the antibody that specifically binds to BIN1 isoform 8 comprises a light chain and a heavy chain selected from the group consisting of:
      (i) a light chain comprising the polypeptide sequences of SEQ ID NO: 8, SEQ ID NO: 9 and SEQ ID NO: 10 and a heavy chain comprising the polypeptide sequences of SEQ ID NO: 11, SEQ ID NO: 12, and SEQ ID NO: 13;
      (ii) a light chain comprising the polypeptide sequences of SEQ ID NO: 18, SEQ ID NO: 19 and SEQ ID NO: 20 and a heavy chain comprising the polypeptide sequences of SEQ ID NO: 21, SEQ ID NO: 22 and SEQ ID NO: 23; and
      (iii) a light chain comprising the polypeptide sequences of SEQ ID NO: 28, SEQ ID NO: 29 and SEQ ID NO: 30 and a heavy chain comprising the polypeptide sequences of SEQ ID NO: 31, SEQ ID NO: 32 and SEQ ID NO: 33; and
   (b) determining a relative total skeletal muscle weight in the human or veterinary subject by comparing the detected level of BIN1 isoform 8 expression and a control level of BIN1 isoform 8 expression from a control human or veterinary subject having a known relative total skeletal muscle weight, wherein a detected level of BIN1 isoform 8 expression less than the control level of BIN1 isoform 8 expression indicates a decreased relative total skeletal muscle weight in the human or veterinary subject as compared to the control human or veterinary subject; and a detected level of BIN1 isoform 8 expression higher than the control level of BIN1 isoform 8 expression indicates an increased relative total skeletal muscle weight in the human or veterinary subject as compared to the control human or veterinary subject.

2. The method of claim 1, wherein the control level of BIN1 isoform 8 expression is the level of BIN1 isoform 8 expression in a normal human or veterinary subject.

3. The method of claim 1, wherein a detected level of BIN1 isoform 8 expression that is lower than the control level in the human or veterinary subject indicates a decreased relative total skeletal muscle mass in the human or veterinary subject as compared to the relative total skeletal muscle mass in a normal human or veterinary subject.

4. The method of claim 1, wherein a detected level of BIN1 isoform 8 expression that is higher than the control level in the human or veterinary subject indicates an increased relative total skeletal muscle mass in the human or veterinary subject as compared to the relative total skeletal muscle mass in a normal human or veterinary subject.

5. The method of claim 3, wherein the human or veterinary subject is diagnosed as having or is suspected of having a disease or condition associated with a decreased relative total skeletal muscle mass as compared to the relative total skeletal muscle mass in a normal human or veterinary subject.

6. The method of claim 5, wherein the disease or condition is selected from the group consisting of multiple sclerosis, atrophy, neurogenic atrophy, a chronic inflammatory condition, and sarcopenia.

7. The method of claim 6, wherein the subject has or is suspected of having sarcopenia.

8. The method of claim 1, wherein the skeletal muscle specific BIN1 isoform comprises SEQ ID NO: 1.

9. The method of claim 1, wherein the antibody that specifically binds to BIN1 isoform 8 is a monoclonal antibody.

10. The method of claim 1, wherein the antibody that specifically binds to BIN1 isoform 8 binds to SEQ ID NO: 2 of BIN1 isoform 8.

11. The method of claim 1, wherein the antibody that specifically binds to BIN1 isoform 8 comprises a light chain light chain comprising the polypeptide sequence of SEQ ID NO: 5 and a heavy chain comprising the polypeptide sequence of SEQ ID NO: 7.

12. The method of claim 1, wherein the antibody that specifically binds to BIN1 isoform 8 comprises a light chain comprising the polypeptide sequence of SEQ ID NO: 15 and a heavy chain comprising polypeptide sequence of SEQ ID NO: 17.

13. The method of claim 1, wherein the antibody that specifically binds to BIN1 isoform 8 comprises a light chain comprising the polypeptide sequence of SEQ ID NO: 25 and a heavy chain comprising polypeptide sequence of SEQ ID NO: 27.

14. A method for detecting skeletal muscle specific bridging integrator 1 (BIN1) isoform 8 in a human or veterinary subject, comprising:
  (a) obtaining a biological sample from a human or veterinary subject, wherein the biological sample is selected from the group consisting of blood, serum and plasma; and
  (b) detecting an amount of BIN1 isoform 8 in the biological sample by contacting the biological sample with an antibody that specifically binds to SEQ ID NO: 2 of BIN1 isoform 8 and detecting the binding between BIN1 isoform 8 and the antibody that specifically binds to SEQ ID NO: 2 of BIN1 isoform 8.

15. The method of claim 14, wherein the antibody that specifically binds to BIN1 isoform 8 is a monoclonal antibody.

16. The method of claim 14, wherein the antibody that specifically binds to SEQ ID NO: 2 of BIN1 isoform 8 comprises a light chain light chain comprising the polypeptide sequence of SEQ ID NO: 5 and a heavy chain comprising the polypeptide sequence of SEQ ID NO: 7.

17. The method of claim 14, wherein the antibody that specifically binds to SEQ ID NO: 2 of BIN1 isoform 8 comprises a light chain light chain comprising the polypeptide sequence of SEQ ID NO: 15 and a heavy chain comprising polypeptide sequence of SEQ ID NO: 17.

18. The method of claim 14, wherein the antibody that specifically binds to SEQ ID NO: 2 of BIN1 isoform 8 comprises a light chain light chain comprising the polypeptide sequence of SEQ ID NO: 25 and a heavy chain comprising the polypeptide sequence of SEQ ID NO: 27.

19. The method of claim 1, wherein the antibody that specifically binds to BIN1 isoform 8 binds to the skeletal muscle-specific phosphoinositol binding domain of BIN1 isoform 8.

20. The method of claim 14, wherein the antibody that specifically binds to SEQ ID NO: 2 of BIN1 isoform 8 comprises a light chain and a heavy chain selected from the group consisting of:
  (i) a light chain comprising the polypeptide sequences of SEQ ID NO: 8. SEQ ID NO: 9 and SEQ ID NO: 10 and a heavy chain comprising the polypeptide sequences of SEQ ID NO: 11. SEQ ID NO: 12, and SEQ ID NO: 13;
  (ii) a light chain comprising the polypeptide sequences of SEQ ID NO: 18. SEQ ID NO: 19 and SEQ ID NO: 20 and a heavy chain comprising the polypeptide sequences of SEQ ID NO: 21. SEQ ID NO: 22 and SEQ ID NO: 23; and
  (iii) a light chain comprising the polypeptide sequences of SEQ ID NO: 28. SEQ ID NO: 29 and SEQ ID NO: 30 and a heavy chain comprising the polypeptide sequences of SEQ ID NO: 31. SEQ ID NO: 32 and SEQ ID NO: 33.

\* \* \* \* \*